United States Patent [19]
Davis et al.

[11] Patent Number: 6,030,406
[45] Date of Patent: Feb. 29, 2000

[54] METHOD AND APPARATUS FOR TISSUE DISSECTION

[75] Inventors: John W. Davis, Mountain View; Timothy B. McFann, Redwood City, both of Calif.

[73] Assignee: Origin Medsystems, Inc., Menlo Park, Calif.

[21] Appl. No.: 09/167,095

[22] Filed: Oct. 5, 1998

[51] Int. Cl.⁷ .................................................. A61B 17/00
[52] U.S. Cl. .......................... 606/198; 604/104; 606/190
[58] Field of Search ..................... 606/191, 198; 604/104, 105; 600/201, 203, 206, 214, 215

[56] References Cited

U.S. PATENT DOCUMENTS

| | | |
|---|---|---|
| 3,667,474 | 6/1972 | Lapkin et al. ........................... 606/198 |
| 5,271,385 | 12/1993 | Bailey . |
| 5,358,496 | 10/1994 | Ortiz et al. . |
| 5,441,044 | 8/1995 | Tovey et al. . |
| 5,450,842 | 9/1995 | Tovey et al. . |
| 5,454,365 | 10/1995 | Bonutti . |
| 5,522,835 | 6/1996 | Tovey . |
| 5,564,615 | 10/1996 | Bishop et al. . |
| 5,577,654 | 11/1996 | Bishop . |
| 5,588,581 | 12/1996 | Conlon et al. . |
| 5,601,224 | 2/1997 | Bishop et al. . |
| 5,607,441 | 3/1997 | Sierocuk et al. . |
| 5,626,587 | 5/1997 | Bishop et al. . |
| 5,634,584 | 6/1997 | Okorocha et al. . |
| 5,656,012 | 8/1997 | Sienkiewicz . |
| 5,662,662 | 9/1997 | Bishop et al. . |
| 5,667,520 | 9/1997 | Bonutti . |
| 5,685,826 | 11/1997 | Bonutti . |
| 5,704,534 | 1/1998 | Huitema et al. . |
| 5,707,390 | 1/1998 | Bonutti . |
| 5,716,325 | 2/1998 | Bonutti . |
| 5,716,352 | 2/1998 | Viola et al. . |
| 5,720,763 | 2/1998 | Tovey . |
| 5,792,178 | 8/1998 | Welch et al. . |

*Primary Examiner*—Michael Buiz
*Assistant Examiner*—William W. Lewis
*Attorney, Agent, or Firm*—Fenwick & West LLP

[57] ABSTRACT

Mechanical retractors for bluntly dissecting tissue at a remote surgical site include extendable element disposed near the distal end of an elongated cannula body with direct mechanical linkage to manual actuators disposed near the proximal end of the cannula body. Individual extendable elements may be arranged in symmetrical or asymmetrical configurations about the central axis of the body for selectively bluntly dissecting bodily tissue in patterns of greater diversity than merely omni-radially as provided by conventional pressurizable balloon tip cannulas.

27 Claims, 17 Drawing Sheets

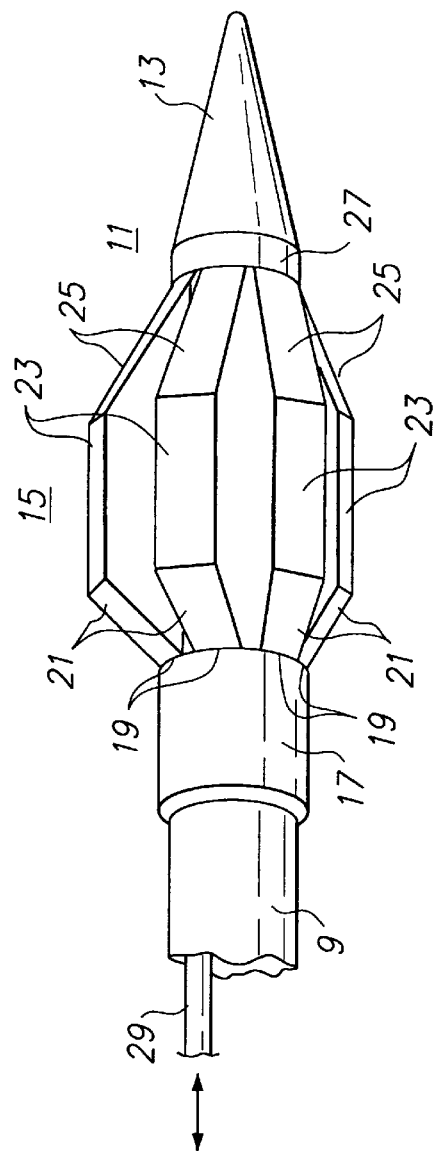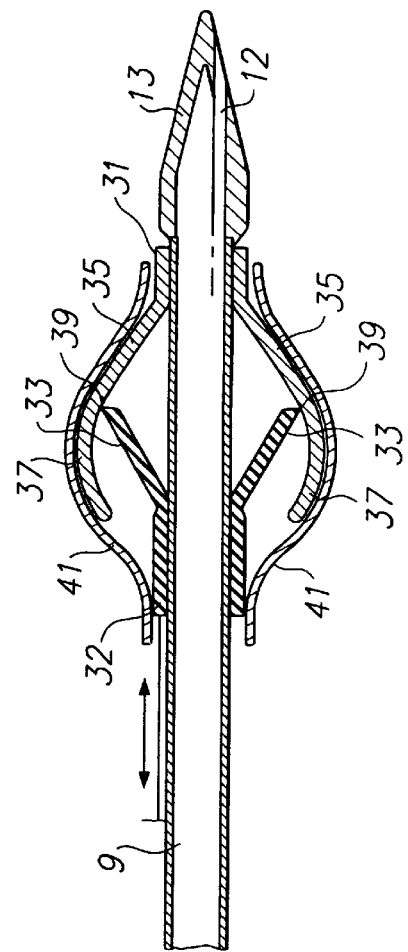

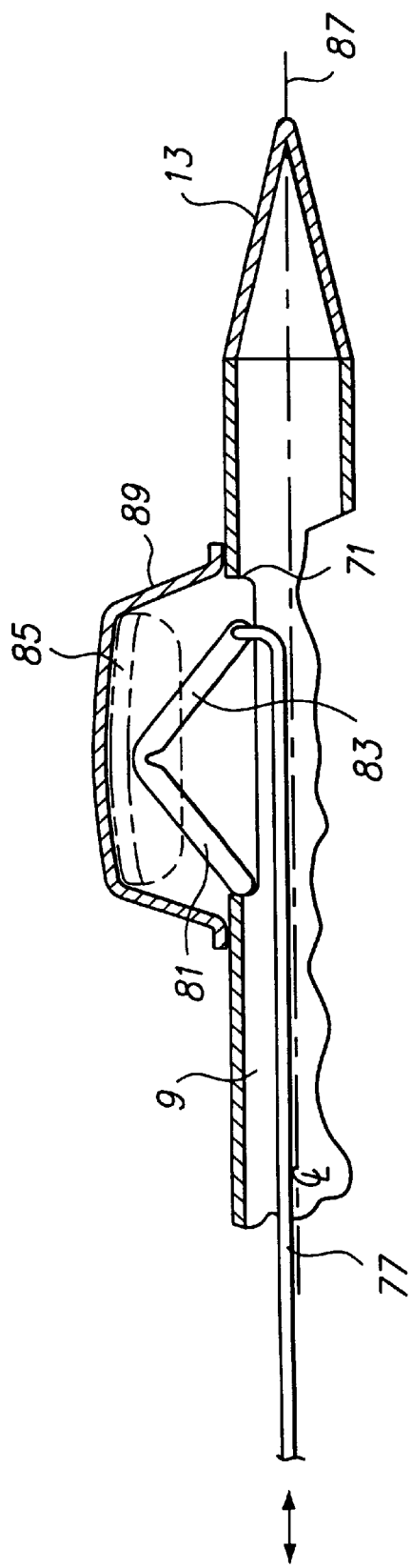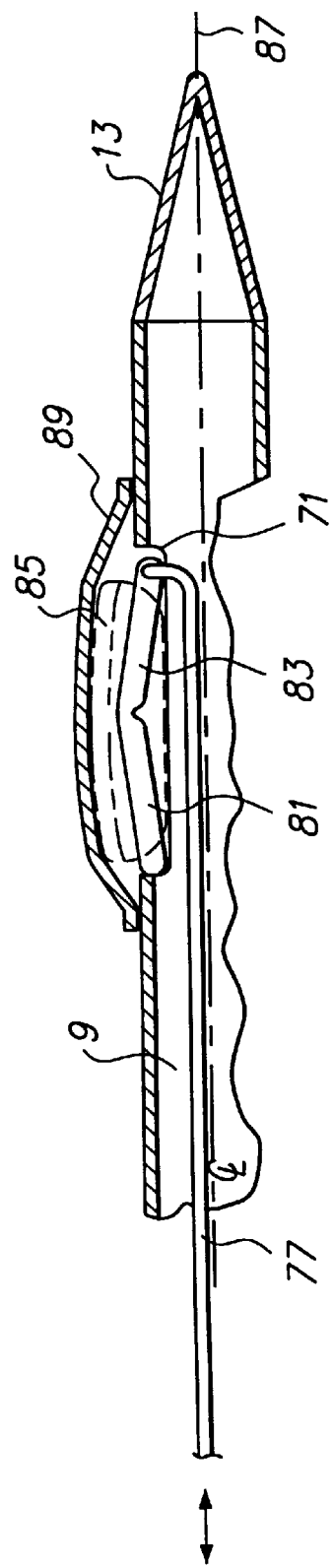

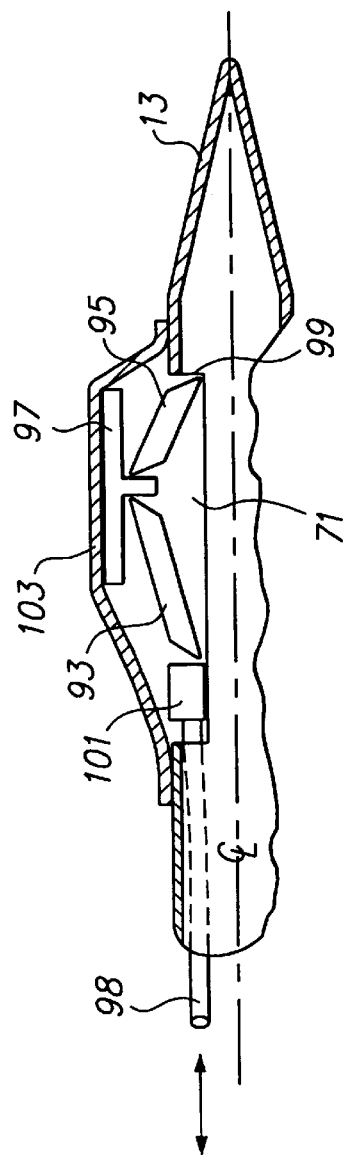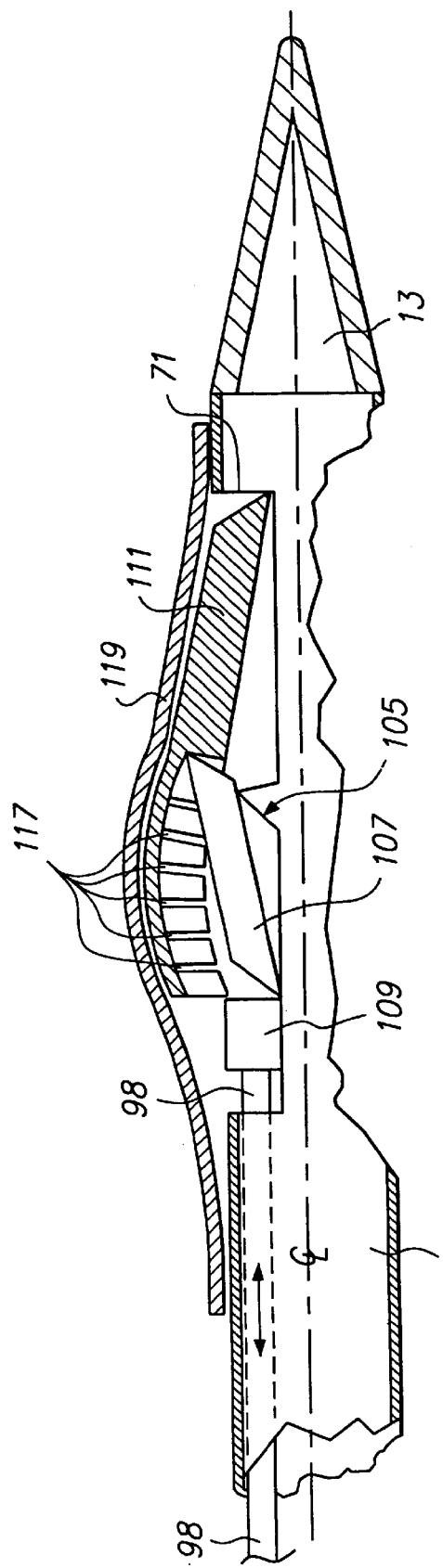

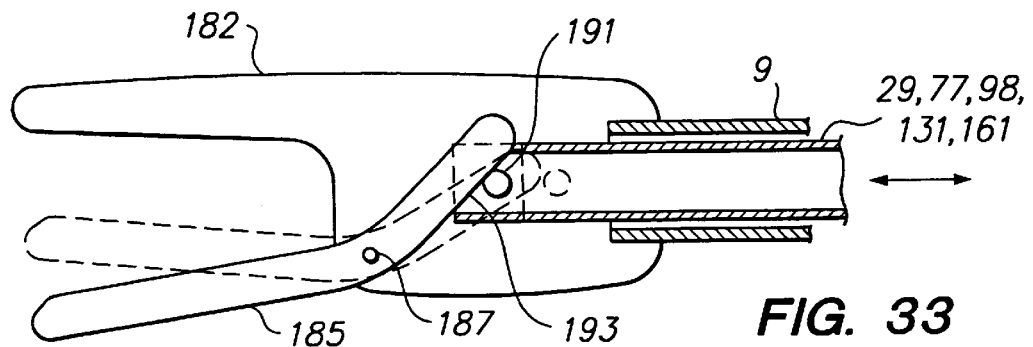
FIG. 33
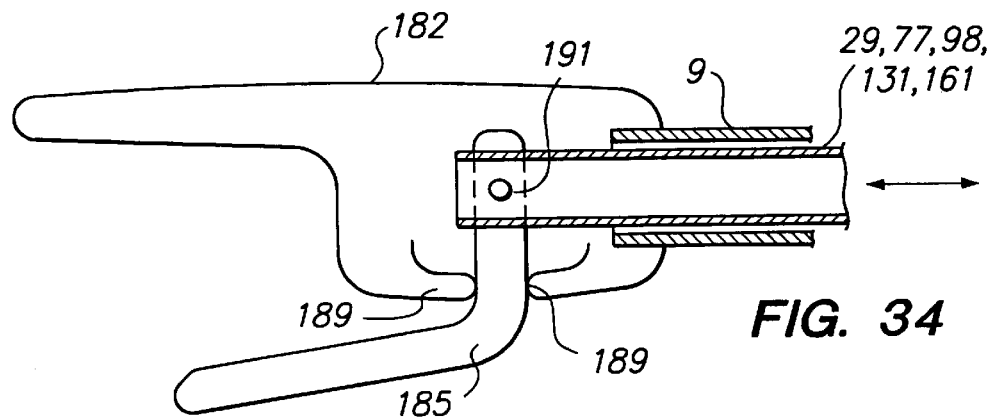
FIG. 34
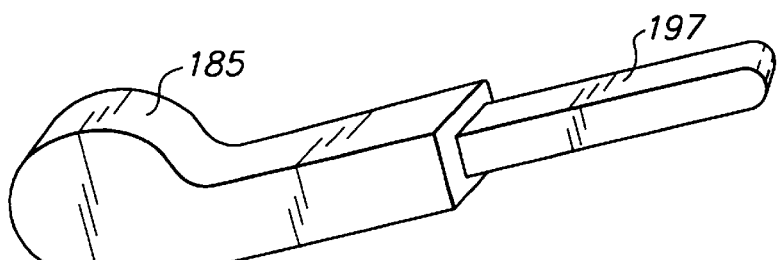
FIG. 35
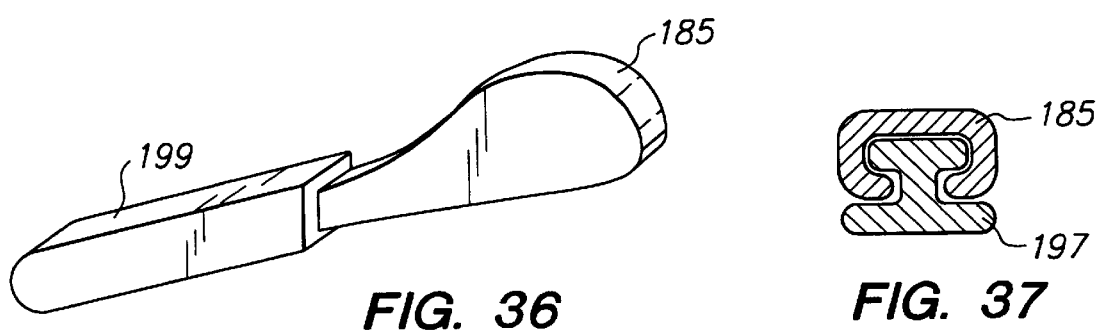
FIG. 36
FIG. 37

SECTION A-A

METHOD AND APPARATUS FOR TISSUE DISSECTION

FIELD OF THE INVENTION

This invention relates to surgical instruments, and more particularly to tissue dissection instruments for forming working cavities in tissue mass via blunt dissection.

BACKGROUND OF THE INVENTION

Certain known tissue dissection instruments are configured for insertion through a percutaneous incision to a layer or tissue plane which can be bluntly dissected via selective expansion or other reconfiguration of the instrument in situ. Such instruments commonly incorporate a tapered tip at a distal end of an elongated body to facilitate penetration of a tissue plane as the instruments is advanced along the plane through the incision. At a selected surgical site, such instruments commonly employ a flexible balloon disposed about the periphery of the instrument near the distal end and tapered tip in order to expand the dimensions, or otherwise reconfigure the instrument under control of applied fluid pressure.

In certain surgical procedures, blunt dissection of tissue by expansion of a peripheral balloon under fluid pressure may promote unnecessary and undesirable symmetry in dissected tissue about the elongated body of the instrument, with associated trauma and reduced control on the surgical procedure. Also, the fluid pressure required to inflate the balloon is usually manually generated using a syringe-like plunger mechanism that may be difficult to manipulate to generate the required pressure.

SUMMARY OF THE INVENTION

In accordance with the present invention, mechanical reconfigurations of a surgical instrument substantially at the distal end of an elongated body via manual controls located at a proximal end greatly facilitate selective shaping of working cavities formed in tissue mass, with associated tactile feel of operative conditions at the remote surgical site adjacent the distal end of the elongated body. Multiple designs of surgical instruments according to the present invention commonly promote re-configurations of the distal end of an elongated body, or cannula, under manual control thereof from a proximal end. Each such reconfigurable cannula includes at least one segment of an elongated body that may be displaced laterally from the elongation or central axis of the body, at least near the distal end thereof, in response to manual manipulations at the proximal end of the body. In this way, working cavities may be bluntly dissected within tissue mass in various shapes and orientations at remote surgical sites removed from a percutaneous incision.

Specifically, one or more movable elements arranged in symmetrical or asymmetrical configurations near the distal end of a cannula are disposed to expand laterally outwardly from the central axis to move adjacent tissue away from the cannula in the course of forming a working cavity at a remote surgical site. Such movable element(s) is/are mechanically linked to manual actuators such as levers, plungers, finger pads, and the like, near the proximal end of the cannula to facilitate manual manipulation of the remotely positioned movable elements, with tactile feedback to the surgeon regarding the operative conditions at the remote surgical site. Various auxiliary appliances such as an endoscope, and blunt-ended, tissue-dissecting tip positioned within, and at the distal end of the cannula, enhance the functionality of the movable elements on a tissue-dissecting cannula.

BRIEF DESCRIPTION OF THE DRAWINGS

FIG. 1 is partial side view of one embodiment of a mechanical retractor according to the present invention;

FIG. 3 is a partial side sectional view of the embodiment of FIG. 2;

FIGS. 11 and 12 are partial side sectional views of another embodiment of the present invention in, respectively, extended and retracted views;

FIG. 13 is a partial side sectional view of another embodiment of the present invention;

FIG. 14 is a partial sectional view of another embodiment of the present invention;

FIGS. 31–34 are partial sectional views of embodiments of hand-operated mechanisms at the proximal end of a cannula for manually controlling retraction and expansion of a tissue retractor at the distal end of the cannula;

FIGS. 35 and 36 are perspective views of hand-operated mechanisms according to the present invention for altering operational leverage;

FIG. 37 is a sectional view of a slidable hand-operated lever for mechanisms of the present inventions.

DETAILED DESCRIPTION OF THE INVENTION

Figure 2:
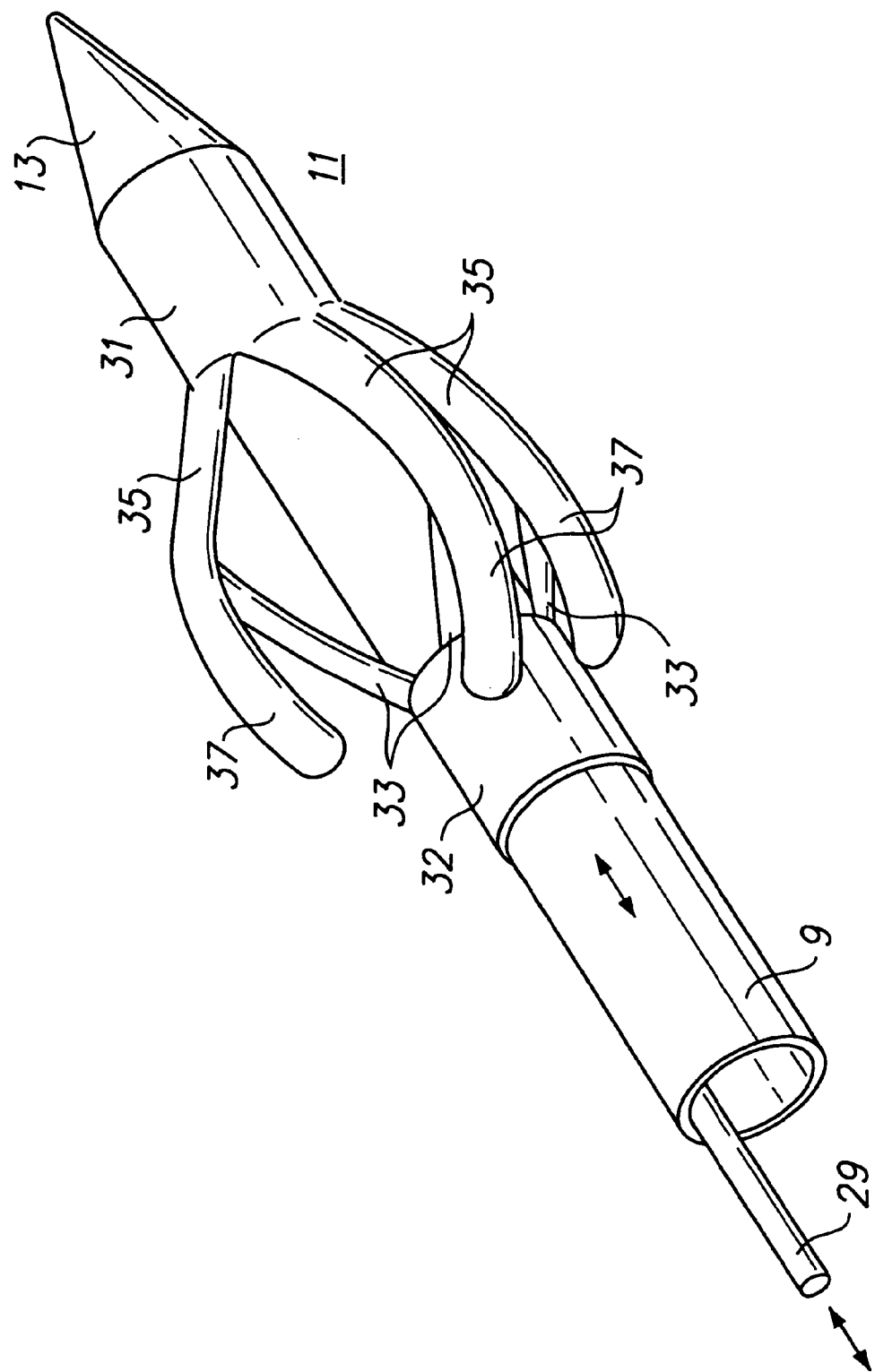
FIG. 2 is a partial perspective view another embodiment of a mechanical retractor according to the present invention.

Referring now to FIG. 1, there is shown one fundamental embodiment of a mechanical retractor according to the present invention including an elongated cannula body 9 having a distal end 11 that may be enclosed by a blunt, tissue-dissecting tapered tip 13. A selectably expandable retractor 15 is disposed about the cannula body 9 near the distal end 11, and includes a slidable ring 17 with hinged attachments 19 at forward edge locations thereon to a set of arms 21 that are therefore disposed to radiate outwardly from the body 9 at the hinged attachments 19. Each arm 21 has hinged attachment to an associated outer segment 23 which, in turn, has hinged attachment to an associated forward arm 25 that, in turn, has hinged attachment to a forward ring 27 on the body 9 near the distal end thereof. The arms 21 and 25 may be of substantially equal lengths. In this configuration, the outer segments 23 are elevated radially outwardly from the body 9 to an extended position in response to translational movement of the ring 17 along the body 9 toward the distal end 11. Similarly, the outer segments 23 are moved radially inwardly to substantially coaxial alignment with the body 9 in a retracted position in response to translational movement of the ring 17 along the body away from the distal end 11 thereof. The assembly of ring 17, arms 21, outer segments 23, arms 25, and forward ring 27, and the associated hinged attachments, may all be formed as by molding a single integrated structure of a resilient polymeric material, or formed of metal components, and may be covered by an elastic sheath (not shown) to inhibit incursion of body tissue at a surgical site into the assembly of movable components. Such integrated structure may be formed to have a relaxed or return state configured either in the extended position as shown, or in the retracted state (not shown) for substantial coaxial orientation along the body 9 near the distal end 11 thereof. One or more lumina within body 9 may house an endoscope, and an actuator rod 29 that is linked to ring 17. The actuator rod 29 extends in slidable fashion within a lumen to the proximal end of the body 9 for facilitating selective translational movement of ring 17 relative to ring 27 from the proximal end of body 9 in order to deploy the outer segments 23 between extended and retracted positions.

Referring now to the perspective view of FIG. 2 and to the sectional view of FIG. 3, there is shown another embodiment of the present invention in which a selectively expandable structure includes a forward ring 31 and rearward ring 32 that are relatively translationally slidable along the body 9 of the cannula to deploy sets of arms 33, 35 that are hinged together and hinged to respective forward and rearward rings 31, 32. Additionally, the forward set of arms 35 hinged to the forward ring 31 include trailing segments 37 that extend rearwardly past the hinged attachment 39 to the rearward set of arms 33. Thus, with the forward ring 31 attached to the cannula body 9 near the distal end 11 thereof, then selective translational movement of the rearward ring 32 along the body 9 relative to the forward ring 31 selectively configures the arms 33, 35 and associated trailing segments 37 between expanded and retracted positions in response to translational movement of the actuator rod 29 that is linked to the rearward ring 32. A resilient sheath 41 is disposed continuously around the assembly over the arms 33, 35 and trailing segments 37 to inhibit incursion of body tissue into the assembly. The arms 33, 35 and trailing segments 37 may be disposed in axially symmetrical or asymmetrical configurations depending, for example, upon the shape or orientation of a working cavity to be formed in body tissue, and the trailing segments 37 may be resiliently shaped to provide relatively smooth contour beneath the sheath 41 in the expanded position, and to provide substantially flat, conformal contour about body 9 in the retracted position. The assembly of forward and rearward rings 31, 32, and sets of arms 33, 35 hinged thereto and to each other, and including the flexible, resilient trailing segments may be integrally formed, for example, by molding of a polymeric material.

The blunt tapered tip 13 (in this embodiment and in all other embodiments illustrated or described herein) may be formed of substantially rigid, transparent bioinert material to provide initial tissue dissection as the body 9 is advanced within bodily tissue, with visualization thereof via an endoscope (not shown) positioned within the body 9 with a field of view through the transparent tip 13. Visualization distortion is significantly reduced using an internal surface of the tip 13 that converges to a sharp point in alignment with the view port of an endoscope, and using an external surface that converges toward a point which is slightly rounded to avoid puncturing vessels or side branches thereof during vessel-harvesting surgical procedures. Optionally, an access port 12 may be provided through the transparent tip 13 to facilitate extension of an endoscopic instrument from within (a lumen in) the body 9 forward of the tip for manipulating tissue within the field of view through the tip 13. Alternatively, the blunt tapered tip 13, or portions thereof, may be removable or hinged to open in order to expose one or more lumens within the body 9 to the working space within bodily tissue for access thereto by Surgical instruments through such exposed lumens.

Figure 4:
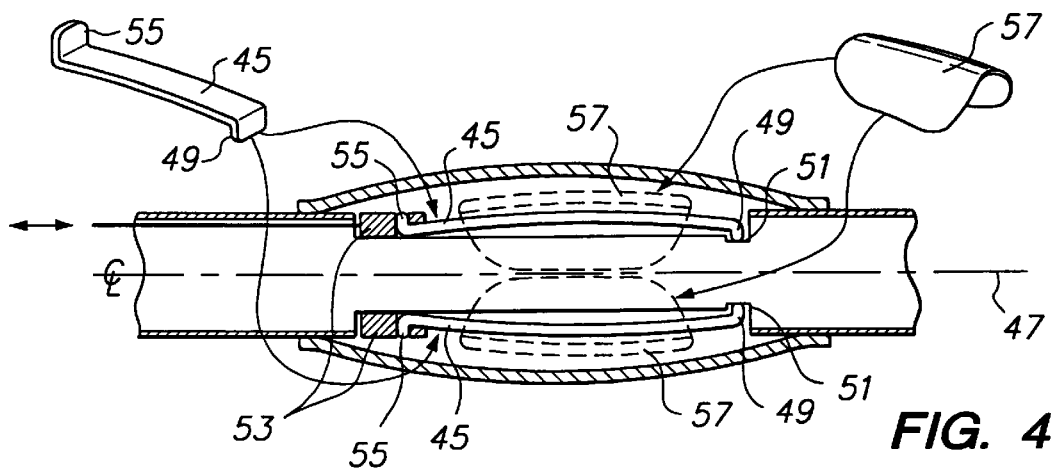
FIG. 4 is a partial side sectional view of another embodiment of the present invention in retracted position.
Figure 5:
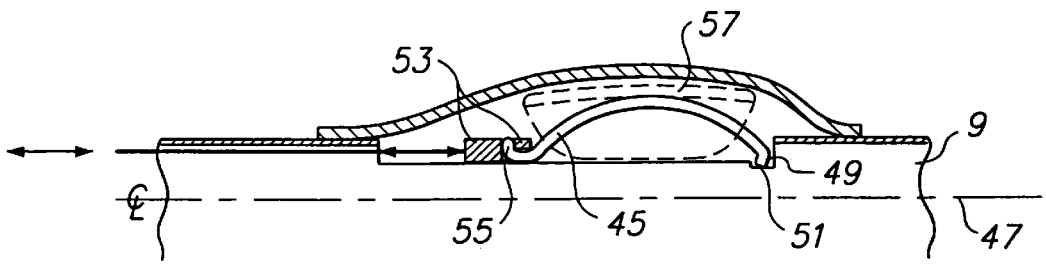
FIG. 5 is a partial side sectional view of the embodiment of FIG. 4 in extended position.

Referring now to the sectional views of FIGS. 4 and 5, there is shown another embodiment of the invention in which the body 9 of the elongated cannula at a location therealong intermediate the distal and proximal ends thereof includes flexible actuators, or flexures, 45 disposed about the surface of the body 9 in longitudinal alignment with the central axis 47 thereof. The flexures 45 may be positioned at angular orientations about the central axis that may be asymmetrically arranged, or symmetrically arranged, as shown in the end views of FIGS. 6 and 7. Each of the flexures 45 is anchored against translational movement relative to the body 9, for example, via an end projection 49 disposed within a detent 51 in the body 9, as shown in FIGS. 4 and 5, and is actuated between expanded position as shown in FIG. 5, and retracted position, as shown in FIG. 4, by translational movement relative to the body 9 of a rearward ring 53 that is linked to the end protrusions 55 of the flexures 45. Thus, selective forward movement of the rearward ring 53 toward the detents 51 flexes the flexures 45 into expanded position, as shown in FIG. 5.

Figure 6:
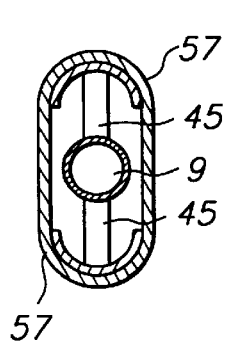
FIGS. 6 and 7 are end views of configurations of the embodiment of FIGS. 4 and 5.
Figure 7:
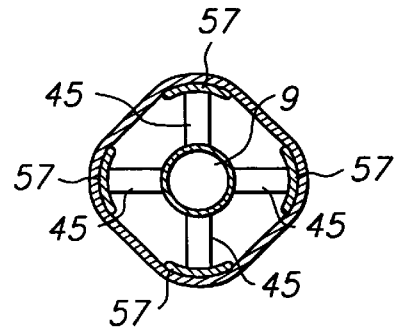

Each flexure 45 supports a saddle-like element 57 that substantially conforms to the outer shape of the body 9, and that extends outwardly in substantial alignment with the body 9 as the associated flexure 45 is flexed into expanded position, as shown in FIGS. 5, 6, and 7. A flexible, resilient sheath 59 covers the assembly to inhibit incursion of body tissue into the assembly at a surgical site, and to provide smooth surface contour and resilient bias toward the retracted position, as desired.

Figure 8:
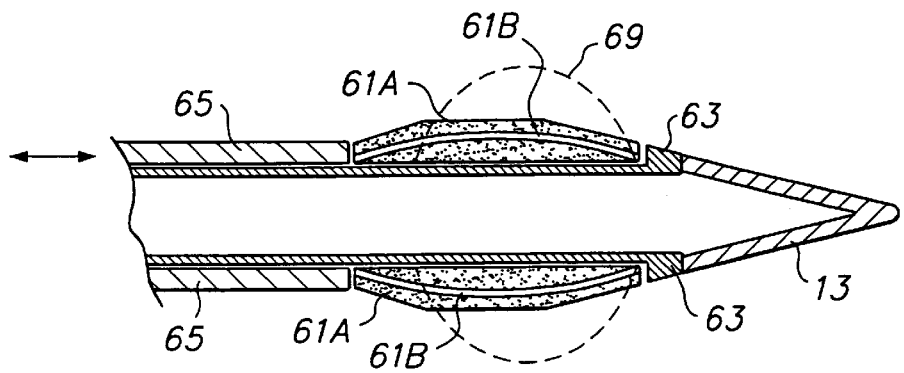
FIG. 8 is a partial side sectional view of another embodiment of a tissue retractor employing an elastomeric expansion member.

Referring now to the sectional view of FIG. 8, there is shown another embodiment of the present invention including a resilient and flexible member 61A disposed as a collar about the body 9 of the cannula near the distal end thereof within a recess having at least a forward stop or abutment 63 disposed to restrain forward translational movement of the element 61A along the body 9. Element 61B may be a flexible actuator, or flexure similar to flexure 45 of FIG. 4 that is embedded or molded into the element 61A for structural support. In this embodiment, the longitudinal dimension of the spring-like flexible, resilient element 61B that is confined within the collar 61A between the abutment 63 and a translationally slidable sleeve or collar 65, may be selectively manually manipulatable from the proximal end of the body 9 (not shown) in order to compress the element 61B into an expanded position with element 61A surrounding the element 61B also being expanded to the expanded position 69 from a retracted or uncompressed position, as shown. The element 61A, 61B thus forms a smooth and substantially continuous contour along and about the body 9 in either the extended position or retracted position, and an overlying sheath may therefore not be required to inhibit incursion of body tissue into the assembly.

Figure 9:
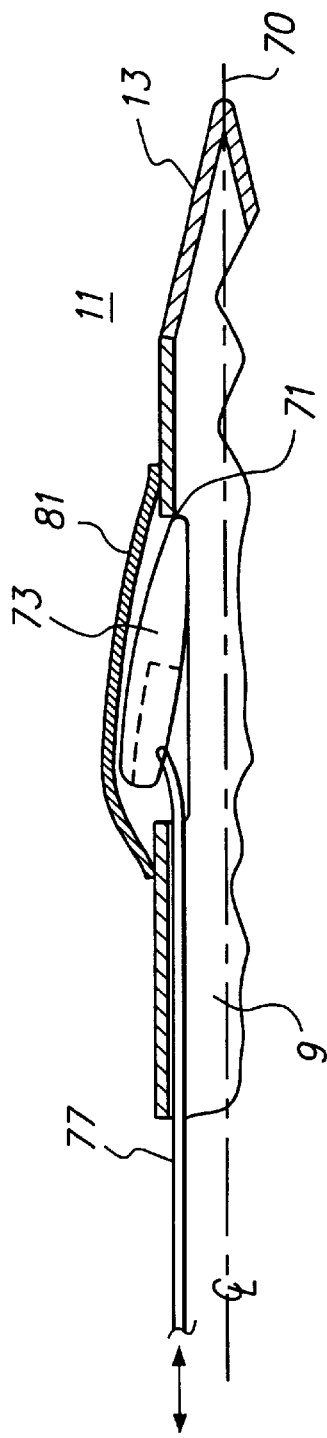
FIGS. 9 and 10 are partial side sectional views of another embodiment of the present invention in, respectively, retracted and extended positions.
Figure 10:
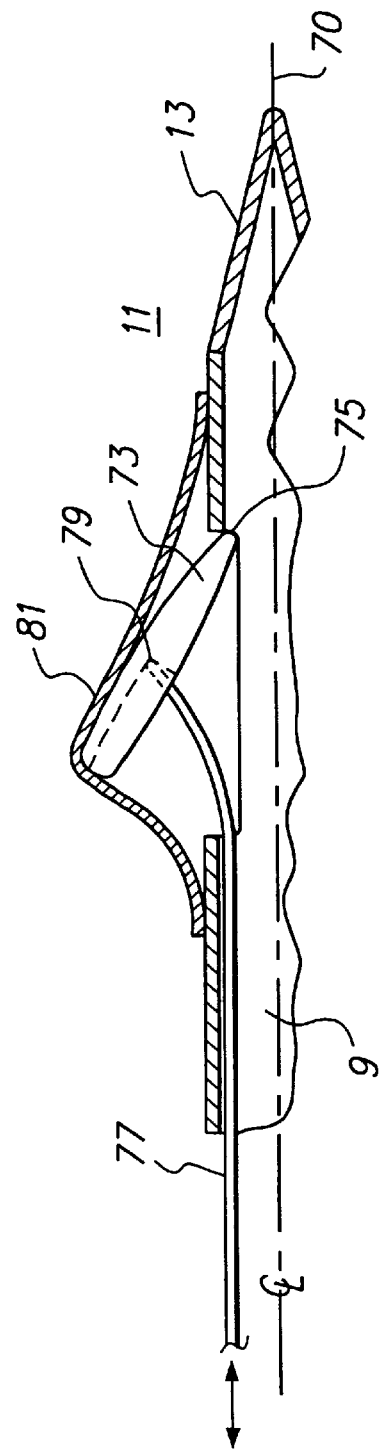

Referring now to the partial sectional views of FIGS. 9 and 10, there is shown another embodiment of a mechanically-retractable, tissue-dissecting cannula according to the present invention having an elongated body 9 with a tapered tissue-dissecting tip 13 disposed at the distal end 11 of the body 9 that may be substantially symmetrical about the center line 70, and with a recess 71 in the surface of body 9 near the distal end 11. An articulating element 73 is disposed within the recess 71 to form a substantially smooth contour with the outer surface of the body 9, and is arranged to elevate at one end thereof about a pivoting abutment 75 at, say, the forward end within the recess 71 in response to translational movement of actuator rod 77 within the body 9. The rod 77 is linked 79 to element 73 in a fixed, or limitedly sliding manner, to provide mechanical advantage for elevating the element 73 into extended position, as shown in FIG. 10, from the retracted position shown in FIG. 9, in response to the actuator rod 77 being slid forward in the element 73. The actuator rod 77 may be resiliently biased into an upward curve, as shown in FIG. 10, to enhance mechanical advantage of elevating the element 73 relative to the abutment 75 toward the extended position. A flexible, resilient sheath 81 may be disposed over the assembly to inhibit incursion of body tissue into the assembly and to provide resilient return force toward the retracted position, as well as to promote smooth surface contours in both the retracted and extended positions.

Referring now to the partial side sectional views of FIGS. 11 and 12, there is shown another embodiment of a mechanically-retractable, tissue-dissecting cannula according to the present invention having a blunt-dissecting tapered tip 13 disposed at the distal end of an elongated body 9 that includes a recess 71 in the surface of the body 9 near the distal end thereof. A pair of arms 81, 83 are each hinged to an upper element 85 that thus moves laterally outwardly from the body 9 toward an extended position in response to angular rotation of the pair of arms 81, 83 toward each other. Specifically, the inner end of arm 81 (that is not hinged to upper element 85) may be referenced to the body 9, as by abutting the proximal boundary of recess 71, or by being hinged thereto, and a corresponding inner end of arm 83 may be translationally movable within the recess 71 in response to translational movement of an actuator rod 77. In this way, for arms 81, 83 of equal (or different) lengths, the upper element 85 is extended outwardly from the body 9 while being maintained substantially parallel thereto. Of course, the arrangement of pairs of arms 81, 83 hinged to respective upper elements 85 may be disposed in symmetrical or asymmetrical angular orientations about the center line 87 of the body 9 to provide one, or two, or more such upper elements 85 that move outwardly to extended position, as shown in FIG. 11, from a retracted position that is substantially contained within the recess 71, as shown in FIG. 12. Each upper element 85 may be shaped as a saddle-like element that substantially conforms to the surface shape of the body 9. Each such pair of arms 81, 83 and associated upper element 85 may be independently operable via individual actuator rods 77, or may all be simultaneously operable in response to translational movement of one actuator rod 77. A flexible, resilient sheath 89 may be disposed over the assembly to inhibit incursion of body tissue into the assembly, and to retain the components in assembled positions, and to provide resilient bias toward the retracted position, as well as to provide smooth surface contours in both the extended and retracted positions.

Figure 17A:
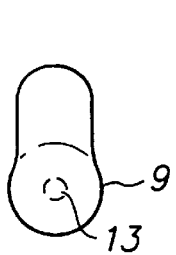
FIGS. 17(*a*), (*b*), and (*c*) are end views of selected configurations of various embodiments such as FIGS. 9–14, and 18.
Figure 17B:
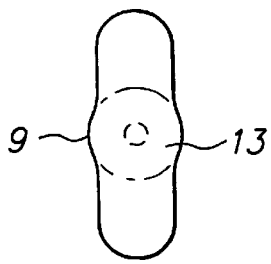
Figure 17C:
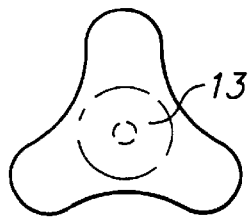

Referring now to the partial sectional view of FIG. 13, there is shown an elongated body 9 having a blunt-dissection tapered tip 13 disposed on the distal end of the body, and having a surface recess 71 positioned in body 9 near the distal end thereof. A pair of arms 93, 95 of same or different lengths are hinged to an upper element 97 and are assembled within the recess 71 to abut a forward end 99 thereof, and to abut a sliding ring or block 101 disposed near the rearward end of the recess 71. In this assembly, translational movement of the sliding ring or block 101 toward the forward end of the recess 71 in response to sliding movements of actuator rod 98 translates into outward movement of the upper element 97 from a retracted position substantially within the recess 71 toward an extended position, as shown in FIG. 13, and toward a more extended position as the arms 93 and 95 angle outwardly from the body 9. The shorter arm 95 of the pair of arms (if the arms are not of equal lengths) may be disposed toward the distal end of the body 9 in order to position the extendable assembly as close as possible to the tapered tip 13 at the distal end of the body 9. The upper element 97 may be shaped as a saddle-like element that substantially conforms to the surface shape of the body near the distal end thereof, and one, or two or more sets of such arms 93, 95 with associated upper saddle-like element may be disposed at symmetrical or asymmetrical angular orientations about the centerline of the body 9, for example, as shown in FIGS. 17(a), (b), or (c). A flexible, resilient sheath may be disposed over the assembly to inhibit incursion of body tissue into the assembly, and to retain the components in assembled positions, and to provide resilient bias toward the retracted position, as well as to provide smooth surface contours in both the extended and retracted positions.

Referring now to the partial sectional view of FIG. 14, there is shown an elongated body 9 with a blunt-dissection tapered tip 13 disposed at the distal end of the body 9, an with a recess 71 positioned near the distal end. An angled ramp 105 is positioned within the recess 71 to cooperate with an associated beveled end of a slidable arm 107 to provide outward force in response to translational, forward movement of a sliding actuator block or ring 109. Another arm 111 is oriented forward of arm 107 within the recess 71 to abut the forward end thereof, and to overlay at least the forward end of arm 107. Arm 111, as shown in perspective view in FIG. 16, may include an underside channel or recess 113 to receive arm 107 therein with the assembly in retracted position, and may include an abutment 115 in the underside channel 113 at a location intermediate the ends of the arm 111 against which the forward end of arm 107 may abut. In this way, the arm 107 may translate forward in response to actuator rod 98 and the associated sliding block or ring 109 to elevate the forward end of arm 107 along ramp 105, and therefore also elevate the forward arm 111 which overlays at least the forward end of arm 107. Such initial elevation then provides mechanical advantage for further elevating the forward arm 111 as arm 107 pushes up against the abutment 115 at the end of the underside channel 113. Further forward movement of the sliding block or ring 109 promotes outward movement of the forward arm 111 toward extended position in manner similar to the illustrations and descriptions set forth above, for example, with respect to FIGS. 2 and 3.

Figure 15:
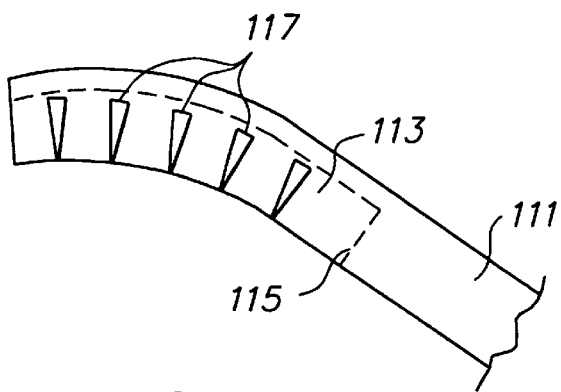
FIGS. 15 and 16 are, respectively, side and perspective views of an arm of the embodiment of FIG. 14.
Figure 16:
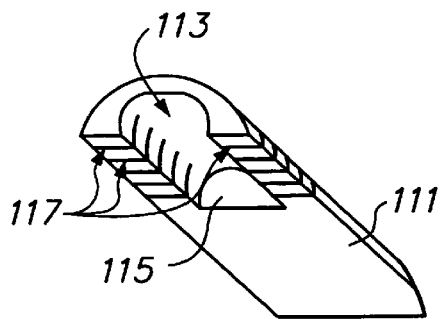

The rearward end of the forward arm 111 may be rendered more flexible by including lateral kerfs or cuts 117 to diminish the cross-sectional thickness at each cut 117, and thereby enhance flexibility near the rearward end of the arm 111, as illustrated in FIGS. 14, 15, and 16. Also, such lateral cuts 117 form distinct shoulders at the underside surface which come into contact at the limits of flexure to inhibit further flexure and to stabilize the trailing edge of arm 111. Of course, one, or two or more sets of such arms 107, 111 and ramps 105 may be disposed at symmetrical or asymmetrical angular orientations about the centerline of the body 9, for example, as shown in FIGS. 17(a), (b), or (c). A flexible, resilient sheath 119 may be disposed over the assembly to inhibit intrusion of body tissue into the assembly, and to retain the component in position, and to provide resilient bias toward retracted position, as well as to provide smooth surface contour in both the retracted and extended positions.

Figure 18:
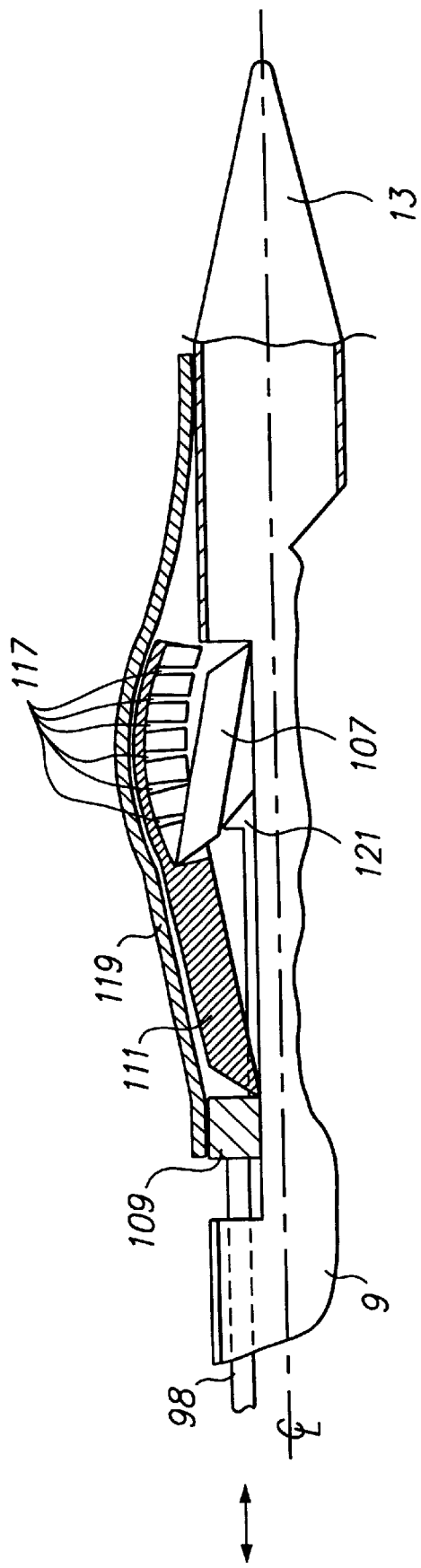
FIG. 18 is a partial section view of another embodiment of the present invention.

Referring now to the partial sectional view of FIG. 18, there is shown an embodiment including an elongated body 9 having a blunt-dissection tapered tip 13 disposed at the distal end of the body 9, and having a recess 71 in the body 9 near the distal end thereof. In this embodiment, substantially similar arms 107, 111 as previously described with reference to FIGS. 14, 15 and 16, are oriented within recess 71 in reverse orientation, and an angled ramp 121 is disposed to engage the beveled end of forward arm 107 to provide elevating force thereto in response to forward sliding movement of the angled ramp 121 provided by sliding movement of the actuator rod 98 coupled to sliding ring or block 109. One or two or more such sets of arms 107, 111 and sliding angled ramp 121 may be disposed at symmetrical or asymmetrical angular orientations about the centerline of the body 9, for example, as shown in FIGS. 17(a), (b), or (c). A flexible, resilient sheath 119 is disposed over the assembly for reasons as previously described herein. The angled ramp 121 and the sliding ring or block 109 may be integrally formed as a single component.

Figure 19:
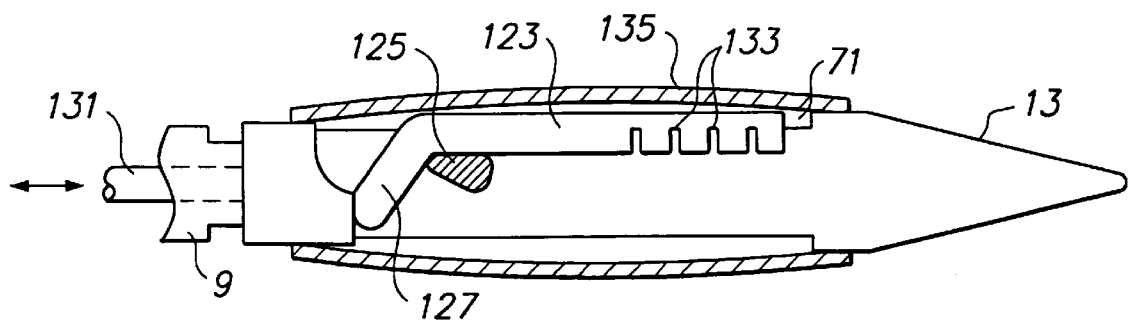
FIG. 19 is a partial side sectional view of another embodiment of the present invention in retracted position.
Figure 20:
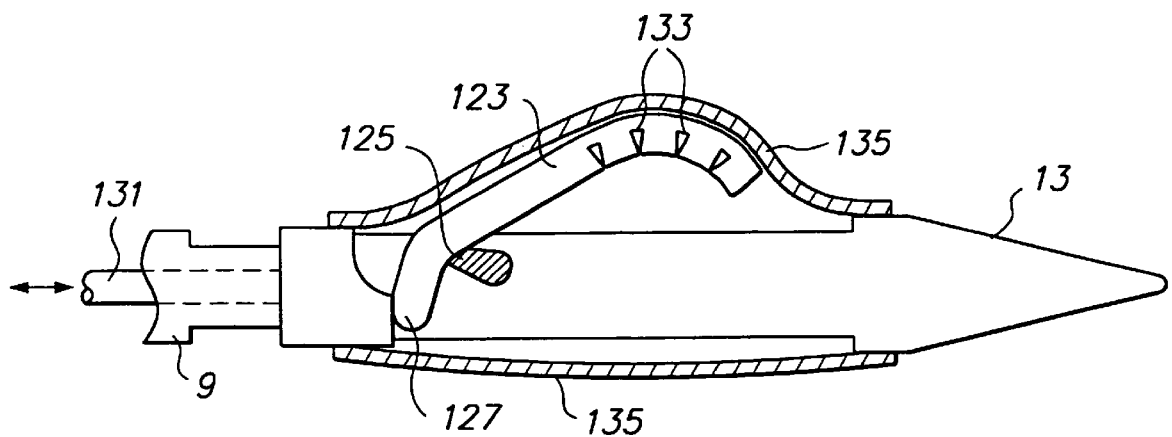
FIG. 20 is a partial side sectional view of the embodiment of FIG. 19 in extended position.

Referring now to the partial side sectional views of FIGS. 19 and 20, there is shown an elongated body 9 with a blunt tissue-dissecting tapered tip 13 disposed over the distal end of the body 9, with a recess 71 in the surface of the body 9 near the distal end thereof. An arm 123 is disposed within the recess 71 against a pivot 125 that is positioned on the body 9 at a selected distance along a lever arm 127 that contacts ring 129 which is translationally slidable along body 9. Specifically, slidable ring 129 is linked to actuator rod 131 that is slidably mounted either outside the body 9 or within a lumen in the body 9 for manual actuation from the proximal end thereof, to urge the ring 129 forward toward the pivot 125 in order to rotate lever arm 127 about the pivot 125. The attached arm 123 therefore extends outwardly from within recess 71, as illustrated in FIG. 20, toward the extended position. The forward portion of the arm 123 may include lateral kerfs or cuts 133 in the underside to diminish the cross sectional thickness thereof, and thereby enhance the flexibility of the forward portion of arm 123. A flexible, resilient sheath 135 may be disposed over the assembly to inhibit incursion of tissue into the assembly, and to provide resilient bias toward the retracted position of the assembly, and to provide smooth surface contour of the assembly in both retracted and extended positions.

Figure 21:
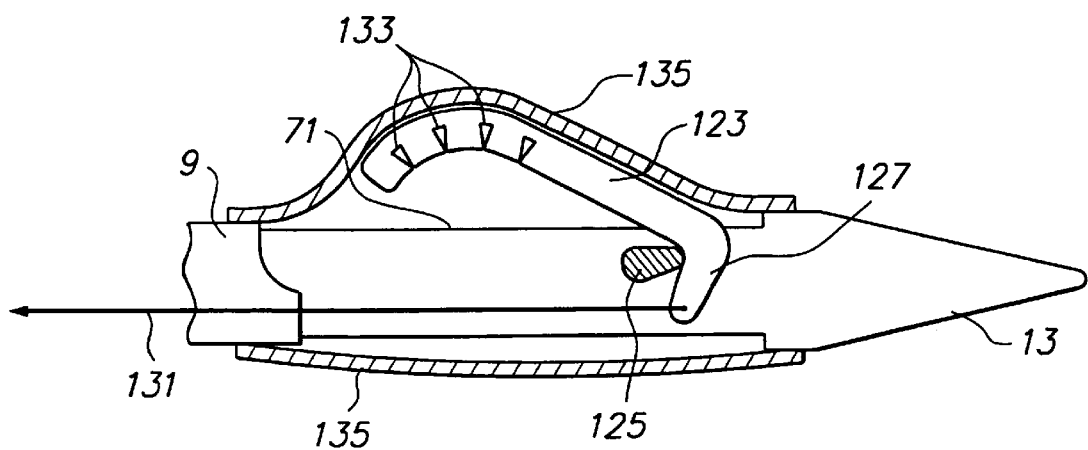
FIG. 21 is a partial side sectional view of another embodiment illustrating a variation of the embodiment of FIGS. 19 and 20.

As illustrated in the partial cross-sectional side view of FIG. 21, another embodiment includes a similar assembly within a recess 71 in the body 9 near the distal end thereof, including an arm 123 disposed against pivot 125 for rotation thereabout toward an extended position as shown in response to pulling on the lever arm 127 via actuator rod 131. The arm 123 may be formed of resilient polymeric material, and may include lateral kerfs or cuts 133 on the underside thereof to diminish cross sectional area of the arm 123 for enhanced flexibility of the rearward end. A resilient, flexible sheath 135 may be disposed over the assembly to inhibit inclusion of tissue into the assembly, and to provide resilient bias toward retracted position, and to provide smooth surface contour in both retracted and extended positions. In each of the embodiments illustrated in FIGS. 19, 20, and 21 one or two or more such arms 123 may be disposed at symmetrical or asymmetrical angular orientations about the centerline of the body, for example, as shown in FIGS. 17(a), (b), or (c).

Figure 23:
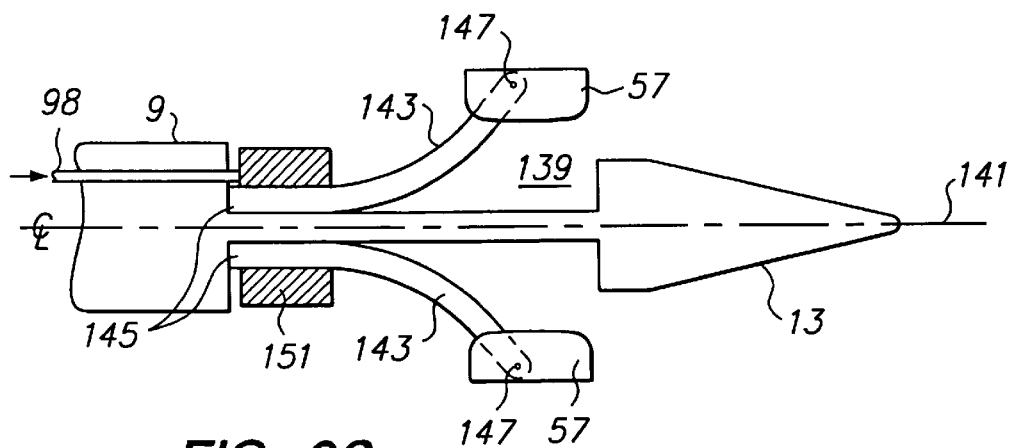
FIGS. 22 and 23 are partial side sectional views of another embodiment in, respectively, retracted and expanded configurations responsive to control of preformed resilient arms.
Figure 22:
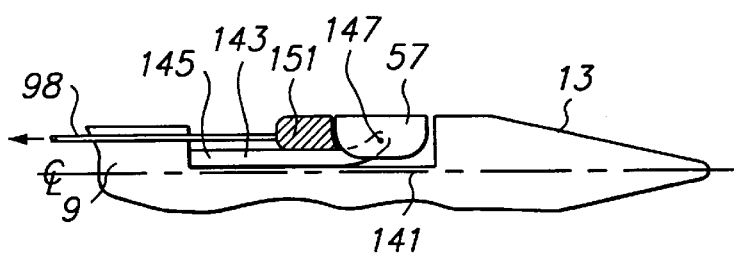

Referring now to the partial sectional views of FIGS. 22 and 23, there is shown a partial cannula body 9 with a tapered tip 13 disposed on the distal end of the body 9. A portion of the body 9 is recessed 139 on opposite sides of an axis 141 of symmetry to receive respective ones of a pair of resilient arms 143 that are preshaped to an outwardly-extending configuration, as shown in FIG. 23. Each of the resilient arms 143 is attached to the body 9 near the proximal ends 145 thereof, and includes a saddle-like element 57 that is pivotally attached 147 to the distal end of each arm 143. The saddle-like elements 57 may be shaped to the outer contour of the body 9 in order to substantially conform the outer shape of the retracted arms 143 and elements 57 (as shown in FIG. 22) to the outer contour of the body 9. A sliding ring 151 is coupled to actuator rod 98 for selectively constraining the resilient, flexible arms 143 in the retracted position, as shown in FIG. 22, in response to the ring 151 and rod 98 being positioned in the forward sliding position, and for selectively releasing the resilient, flexible arms into expanded position, as shown in FIG. 23, in response to the ring 151 and rod 98 being positioned in the rearward sliding position. Of course, the assembly may be covered by a flexible, resilient membrane (not shown) to inhibit incursion of body tissue into the assembly.

Figure 24:
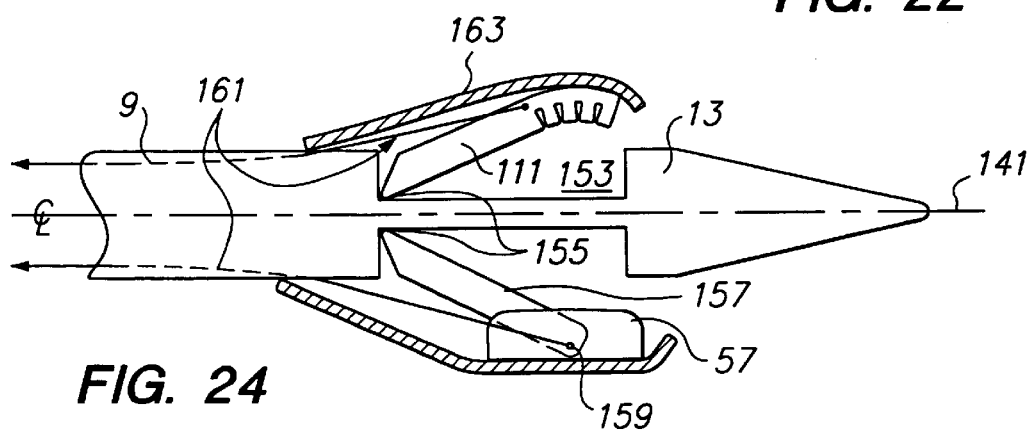
FIG. 24 is a partial side sectional view of a composite of embodiments of the present invention illustrating control of operation between retracted and expanded configurations in response to tension wires.

Referring now to the partial cut-away sectional view of FIG. 24, there is shown a composite illustration of alternate embodiments of the present invention that may be singly or symmetrically arranged in corresponding recesses 153 near the distal end of a cannula body 9 about central axis 141. In one such embodiment, an arm 111 such as illustrated and described with reference to FIG. 16 herein may be pivoted 155 in the proximal end of the recess 153, and in another such embodiment, an arm 157 having a saddle-like element 57 pivotally attached 159 thereto may also be pivoted 155 in the proximal end of the recess 153. In each such embodiment, the arm 111, 157 is elevated to expanded position, as shown, in response to an actuating wire 161 pulling the arm against the pivot 155 from an elevation relative to the central axis 141 that is above the pivot 155. The arms 111, 157, of whichever configuration, may be positioned into retracted position within the recess 153 (not shown) by relaxing tension on the actuating wires 161. Resilient flexible membrane 163 may be disposed over the assembly to provide resilient restoring force toward the retracted position and to inhibit incursion of body tissue into the assembly.

Figure 25:
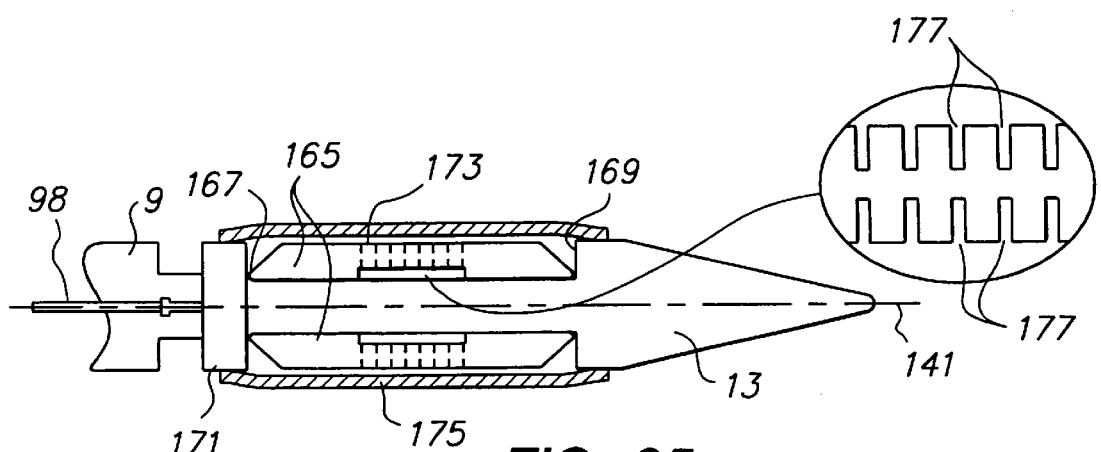
FIGS. 25 and 26 are partial side sectional views of an embodiment in, respectively, retracted and expanded configurations.
Figure 26:
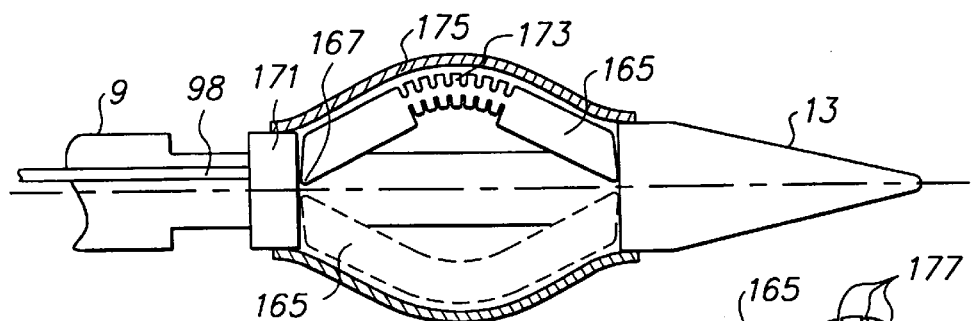

Referring now to FIGS. 25 and 26, there are shown partial, cut-away sectional views of another embodiment of the present invention in, respectively, retracted and expanded positions. The cannula body 9 includes a tapered tip 13 on the distal end thereof, and includes a recess near the distal end to contain one or more arms in retracted position substantially within the outer contour of the body 9. Each such arm includes pivots 167, 169 at opposite ends thereof that are positioned to abut the distal end of the recess, and the sliding ring 171 remote from the distal end. As the ring 171 is slidably, selectively positioned toward the distal end of body 9, the arms 165 with flexible central regions 173 are urged to deflect outwardly, as shown in FIG. 26, toward the expanded position. A resilient, flexible membrane 175 is disposed over the assembly to inhibit incursion of body tissue into the assembly, and to provide resilient restoring force toward the retracted position, as shown in FIG. 25. In each of the embodiments disclosed herein, translational movement of a component in the assembly at the distal end of the body 9, for example, of ring 171 in the embodiments of FIGS. 25 and 26, in order to configure the assembly in the expanded condition may be accomplished through translational or rotational movement of the actuator rod or wire within the body 9. Rotational movement of such actuator may be coupled via a helical groove or lead screw and a follower in conventional manner to translate a component in the assembly at the distal end of the body 9 in response to rotation of the actuator rod to configure the assembly in expanded and retracted positions.

Figure 27:
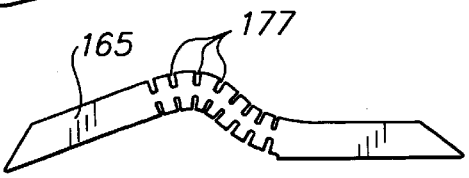
FIGS. 27–30 are pictorial illustrations of flexible retractor arms.
Figures 28, 29:
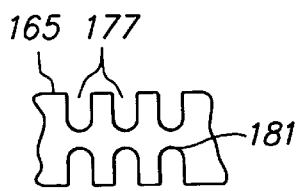
Figure 30:
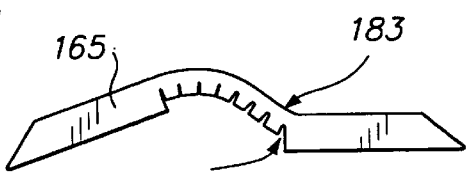

The flexible central regions 173 of the arms 165 may be configured in manner similar to the illustrations and descriptions with respect to FIGS. 15 and 16 herein, with additional lateral kerfs or cuts 177 on the outer surface, as shown in FIGS. 27, 28, and 29. Such kerfs on both under surface and outer surface of an arm reduces the cross sectional area of a resilient, flexible material in order to enhance the outward lateral expansion of the region 173 in response to the forward sliding movement of the ring 171 without materially altering the compressibility of the arm between pivots 167, 169. Additionally, the kerfs 177 may be controlled in width to provide mechanical stability and rigidity of the arm in curved configuration resulting from the opposite walls or sides of each kerf 177 coming together, or contacting, as shown on the underside of arm 165 in FIG. 26. Similar mechanical stability and rigidity is attained as the sides of kerfs in the outer surface of arm 165 contact to inhibit further flexure and restrict "S" shape lateral expansion of an arm 165, as shown in FIG. 27. The roots or bases of the lateral kerfs 177 may conclude in a cylindrical recess 179, as shown in FIG. 28, or in a smoothly curved recess 181, as shown in FIG. 29. The kerfs 177 may recur at a selected depth and periodicity along a central portion of the length of arm 165 on both the outer and under surfaces thereof, or may recur at different depths and periodicities on such outer and under surfaces as may be required to control flexure of the arm 165 in response to slidable positioning of the ring 171. In this way, undue stress upon the remaining cross section 183 of an arm 165 due to excessive or concentrated bending, as illustrated in FIG. 30, can be greatly reduced.

It should be noted that the embodiments of assemblies near the distal end of the body 9, as disclosed herein, may be formed substantially on and around the generally tubular surface of the body 9 without requiring any recess (for example, of the type described with reference to recess 71).

Figure 31:
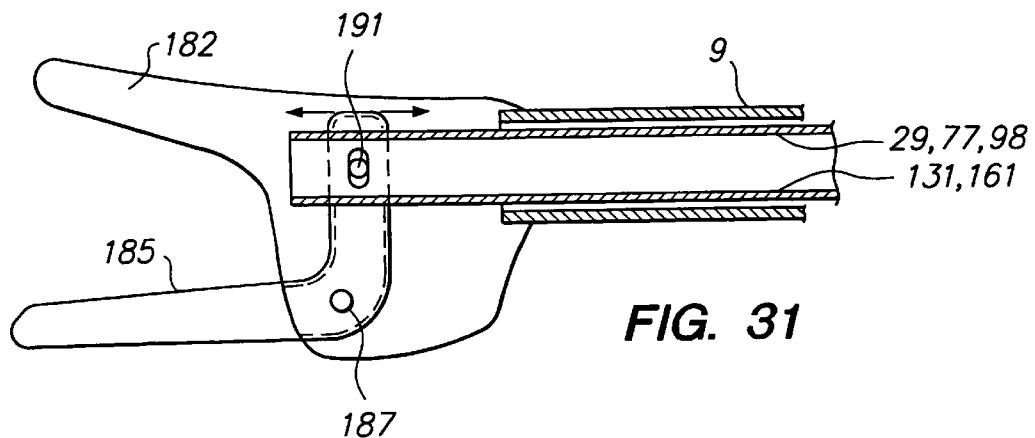
Figure 32:
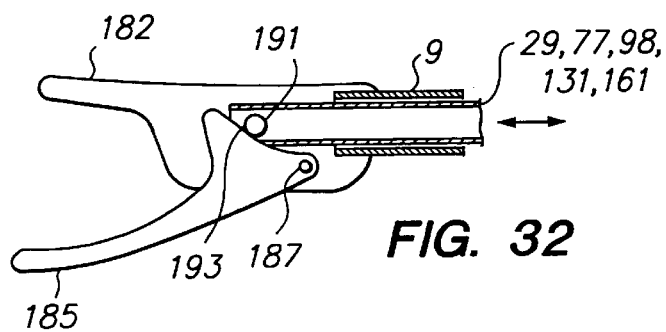

In each of the embodiments of a tissue retractor illustrated and described above, an actuator rod or wire 29, 77, 98, 131, 161 controls selective configuration of the retractor elements between expanded and retracted positions near the distal end of a cannula body 9. With reference now to FIGS. 31–34 there are shown various configurations of hand-operated mechanisms disposed on the cannula body 9 near the proximal end thereof for effecting controlling motion of an actuator rod or wire 29, 77, 98, 131, 161. Such motion of the actuator rod or wire may be translational or rotational, or combined translational and rotational motions as desired. In each such mechanism a housing 182 is attached to the cannula body 9 near the proximal end thereof, and supports a trigger-like element 185 for rotation relative to the housing 182. In the embodiments of FIGS. 31, 32, and 33 the trigger-like elements 185 are privotally attached 187 to the housing 182 for rotation about such privotal attachment in response to manual squeezing together of the trigger 185 and body 182. In the embodiment of FIG. 34, a pivotal constraint for rotation of the trigger 185 relative to the housing 182 is provided by abutments 189 on the housing 182 slidably engaging the trigger 185. Such rotational motion of the trigger 185 about its pivot 187, 189 is converted to translational motion of the actuator rod, tube, or wire 29, 77, 98, 131, 161 via a lever arm attributable to the offset of the pivot 187, 189 from the slide axis of the actuator rod or wire 29, 77, 98, 131, 161. In the embodiments of FIGS. 31 and 34, an actuator pin 191 connects the lever arm to the actuator rod, tube, or wire. In the embodiments of FIGS. 32 and 33, a ramp surface 193 slidably engages the actuating pin 191 attached to the actuator rod or wire. In each such embodiment, the actuating pin need not penetrate through the actuating rod (which may be hollow to receive an endoscope or other instrument therein), but instead need only protrude (or penetrate through the wall of the actuator rod) from the outer side surfaces of the actuating rod to engage corresponding segments of the lever arm, disposed as a yoke of the trigger element 185, on each side of the actuator rod 29, 77, 98, 131, 161. Of course, pulling force rather than pushing force can be achieved on an actuator road or wire in response to manual squeezing of the trigger relative to the housing simply by positioning the pivot for the trigger at a location on the housing that is remote from both the trigger and actuator rod or wire (e.g. above the actuator rod or wire in the illustrations), rather than by positioning the pivot at a location intermediate the trigger and actuator rod or wire, as shown. Selected mechanical advantages can be attained via selected ratios of lever arms about a pivot therefor, and via selected ramp surfaces 193, in conventional manner. Additional mechanical advantage can be attained by selectively slidably extending the length of the trigger element 185 with respect to the pivot 187, 189 therefor, as shown in FIGS. 35 and 36, via internal or external slide members 197, 199 on the trigger element 185. Alternatively, any interlocking, slidably-extendable configuration of trigger element 185, as illustrated in the sectional view of FIG. 37, may be used. And, actuators 29, 77, 98, 131, 161 may be disposed outside or within the body 9.

Figure 38:
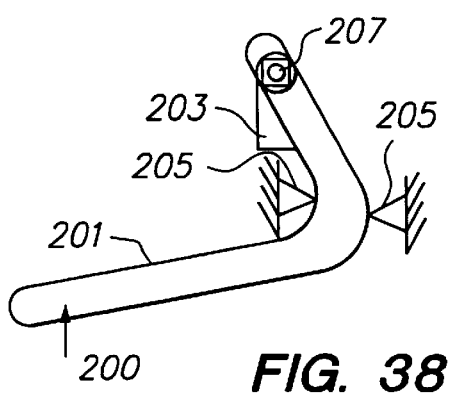
FIG. 38 is a side view of a yoke-shaped trigger or hand-operated lever according to one embodiment of the present invention for operation with a sliding pivot.
Figure 39:
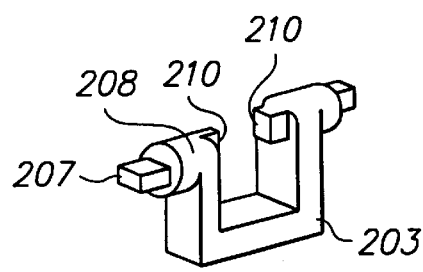
FIG. 39 is a perspective view of a carriage for engagement within the yoke-shaped trigger of FIG. 38.
Figure 45:
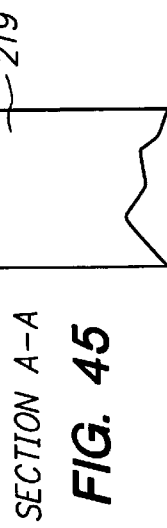
FIG. 45 is an end sectional view of the assembly of FIG. 44.

In FIG. 38, there is shown a side view of a yoke-shaped trigger element 201 for operation with a carriage 203, as shown in perspective view in FIG. 39. In these embodiments, yoke-shaped trigger element 201 rotatably supports the carriage 203 within the yoke upon bearing surfaces 208, and trigger element 201 may slidably pivot against pivots 205 attached to a surrounding housing. Square protrusions 207 of smaller dimensions than the bearing surfaces 208 may protrude through mating apertures in trigger element 201 to engage longitudinal channels 225 in a surrounding body 223, as later described herein, for example, with reference to FIG. 45. The inner protrusions 210 on carriage 203 may engage mating slots or apertures in an actuating rod for longitudinal translation thereof in response to manual actuation, or squeezing, of the trigger element 201 in the direction 200 toward a surrounding housing.

Figure 40:
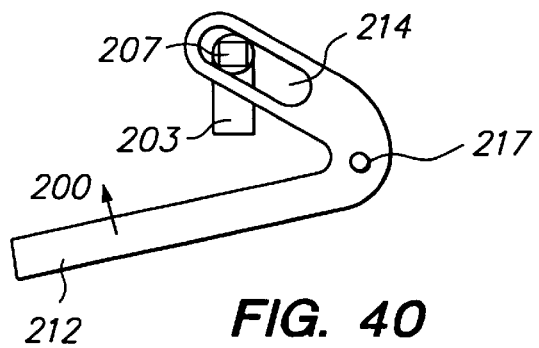
FIG. 40 is a side view of a yoke-shaped trigger similar to the embodiment of FIG. 38 for operation with a fixed pivot within a low elevational profile.
Figure 41:
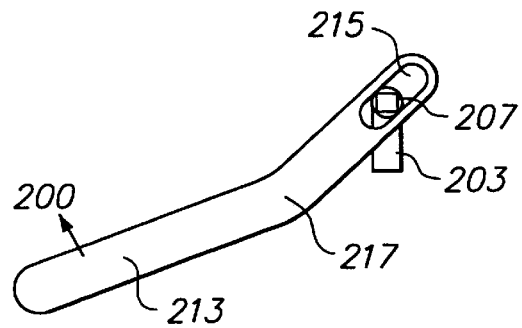
FIG. 41 is a side view of another embodiment of a yoke-shaped trigger for operation with a fixed pivot within a low elevational profile.

In the alternative embodiments of a trigger element 212, 213 illustrated in FIGS. 40, 41, similar yoke-shaped structure may be operated about fixed pivots 217, and support a carriage 203 for slidable movement within mating slotted apertures 214, 215. In this way, the square protrusions 207 may translate along longitudinal channels in a surrounding body or housing 223 in response to squeezing movement of the trigger element 212, 213 in the direction 200 toward the surrounding housing. The embodiments of FIGS. 40, 41 facilitate reducing the elevational profile of a surrounding housing 223 relative to the trigger element 212, 213 for more compact instrumentation in the hand of an operating surgeon.

Figure 42:
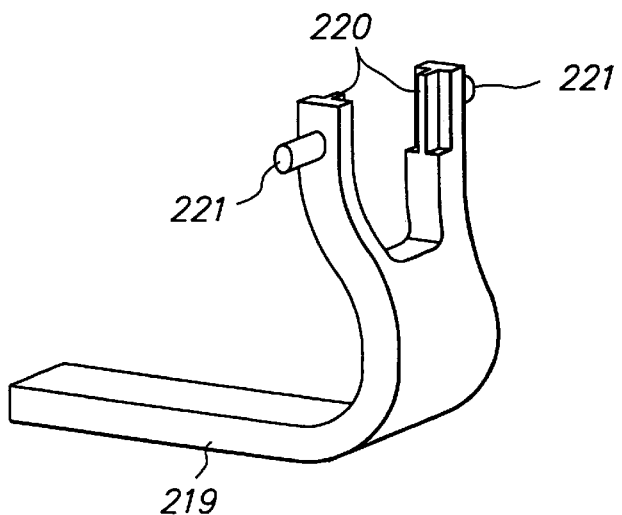
FIG. 42 is a perspective view of another embodiment of a yoke-shaped trigger.
Figure 43C:
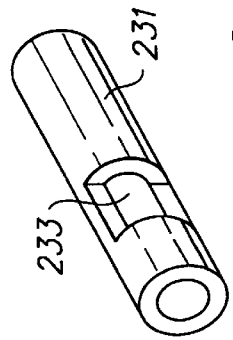
FIG. 43C is a partial perspective view of an actuator rod in the embodiment of FIG. 43A.
Figure 44:
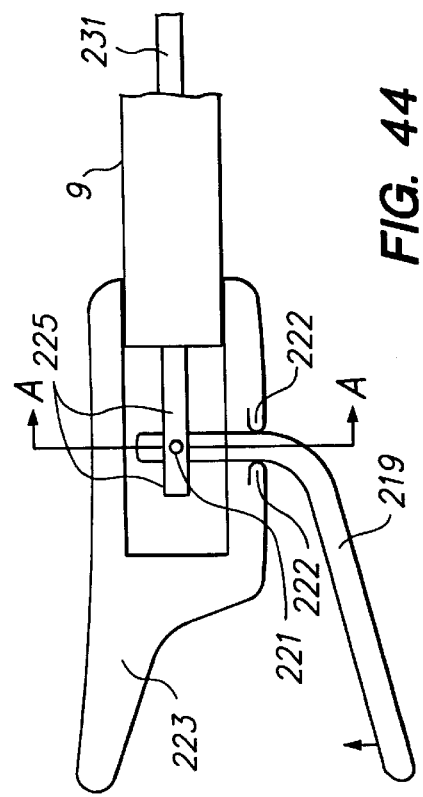
FIG. 44 is a partial side view of one embodiment of a hand-operated mechanism on the proximal end of a cannula.

Referring now to FIGS. 42 and 44, there are shown, respectively, a perspective view of a yoke-shaped trigger element 219 arranged for sliding pivotal movement about sliding pivotal joint 222 relative to a surrounding housing 223, and a cutaway side view in FIG. 44. Specifically, outer protrusions 221 may support the trigger element 219 within longitudinal channels 225 within the inner side walls of the surrounding housing 223, and be longitudinally slidable therealong in order to translate the pivoted movement of the trigger element 219 into longitudinal sliding movement of an actuator rod 231. The inner vertical protrusions 220 are thus positioned to engage slots in an actuator rod, as shown in FIGS. 43A and 43C.

Figure 43B:
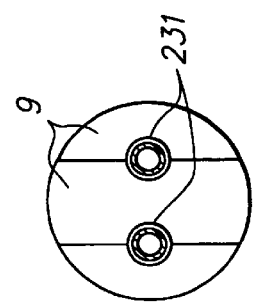
FIG. 43B is an end sectional view of the cannula of FIG. 43A.
Figure 43A:
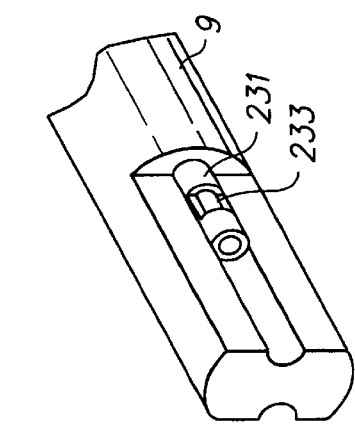
FIG. 43A is a partial perspective view of the proximal end of a cannula having a slidable actuator rod therein for actuation by a yoke-shaped trigger.

Referring now to the perspective view in FIG. 43A and to the sectional view in FIG. 43B of a proximal end of a cannula body 9, and to the perspective view in FIG. 43C of an actuating rod in FIG. 43A, there are shown structures for slidably translating the actuator rod(s) 231 within the body 9 of the cannula. The actuator rod 231 (which may be the actuator rod 29, 77, 98, 131, 161 of embodiments previously described herein) includes notches 233 formed in a portion of the diameter (or thickness) of the rod to receive the inner protrusions 220 in vertical sliding engagement therein. Thus, pivoted movement of the trigger element of FIG. 42 within the sliding pivots 222 transforms into translational movement of the actuator rod(s) 231 within the cannula body 9 through the engagement of the inner protrusions 220 of the trigger element 219 with the notch 233 in the actuator rod 231, as illustrated in the sectional view of FIG. 45.

Figure 46:
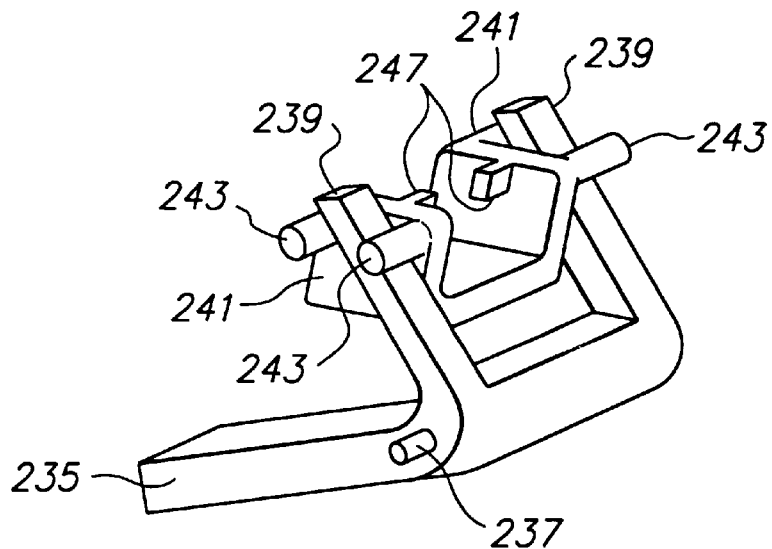
FIG. 46 is a perspective view of a trigger and carriage mechanism for operation on a fixed pivot.

Referring now to the perspective view of FIG. 46, there is shown a yoke-shaped trigger element 235 that is configured for fixed-pivot attachment at pivot pin 237 to a surrounding housing. Each arm 239 of the yoke actuates the carriage 241 that is supported in sliding engagement therewith. Specifically, the carriage 241 includes a spaced pair of outer protrusions 243 that slide along an arm 239 and that also engage respective longitudinal channels within a surrounding housing to retain the carriage 241 in the illustrated orientation during longitudinal translation in response to rotation of the trigger element 235 about the pivot pin 237. The inner protrusions 247 thus translate in longitudinal orientation, and engage the notches 233 in the actuator rod(s) 231, as shown in FIGS. 43A and 43C, to translate the actuator rod(s) 231 within the cannula body 9 in response to manual squeezing of the trigger element 235 toward a surrounding housing 223, as shown in FIG. 44.

Figure 47A:
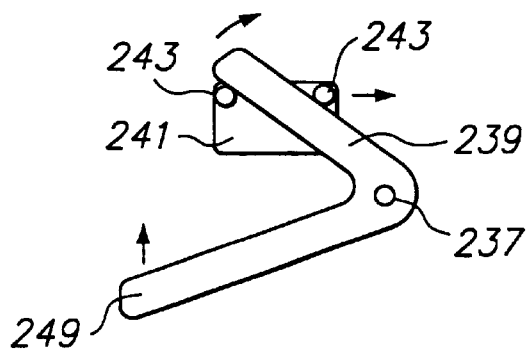
FIGS. 47A, B are side views of trigger and carriage mechanisms similar to the embodiment of FIG. 46 for operation within a low elevational profile.
Figure 47B:
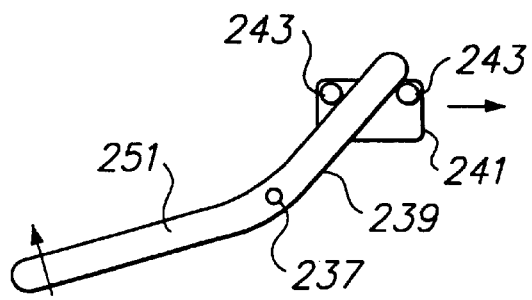

Referring now to the trigger elements 249, 251 shown in the side views of FIGS. 47A and 47B, respectively, these trigger elements may include yoke-shaped structures, as illustrated in FIG. 46, for translating the movement of carriage 241 in response to movement about the pivot pin 237. The yoke-shaped arms 239 of each trigger element 249, 251 are oriented to operate with lower elevational profile to translate the carriage 241 (and an actuator rod 231 coupled thereto) in response to rotational movement of the trigger element about the pivot pin 237.

Figure 48A:
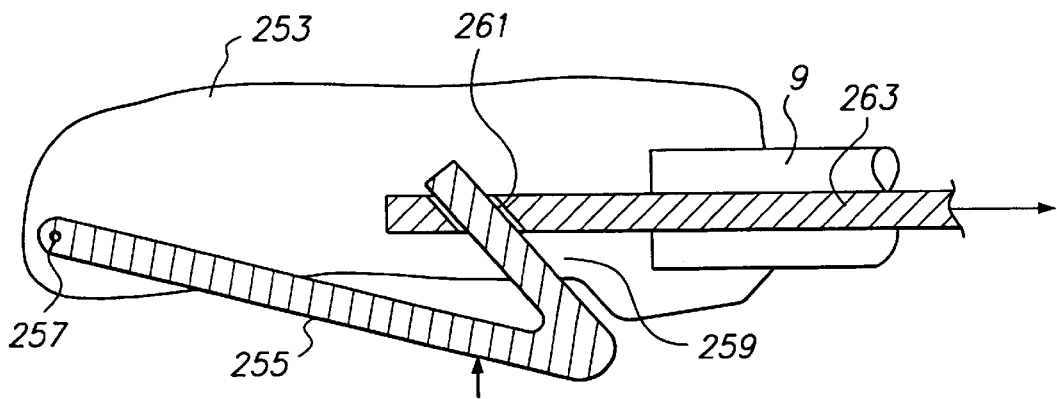
FIG. 48A is a partial cutaway sectional view of one embodiment of a hand-operated mechanism on a proximal end of a cannula.
Figure 48B:
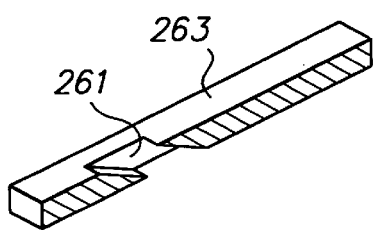
FIG. 48B is a perspective sectional view of a coupling slot (or aperture) in an actuator rod according to the present invention.

Referring now to FIG. 48A, there is shown another embodiment of a manual actuator at the proximal end of the cannula body 9. Housing 253 is attached to the body 9 and includes a trigger element 255 pivotally attached 257 thereto. The trigger element 255 includes a camming portion 259 that is slanted relative to a radius from the pivot 257 and that engages a slot 261 in actuator rod 263 that is more clearly illustrated in the perspective view of FIG. 48B. In this embodiment, manually squeezing the trigger element 255 toward the housing 253 translates to sliding engagement of the camming portion 259 in the slot 261 in actuator rod 263 which, in turn, causes translational movement of the rod 263.

Figure 49:
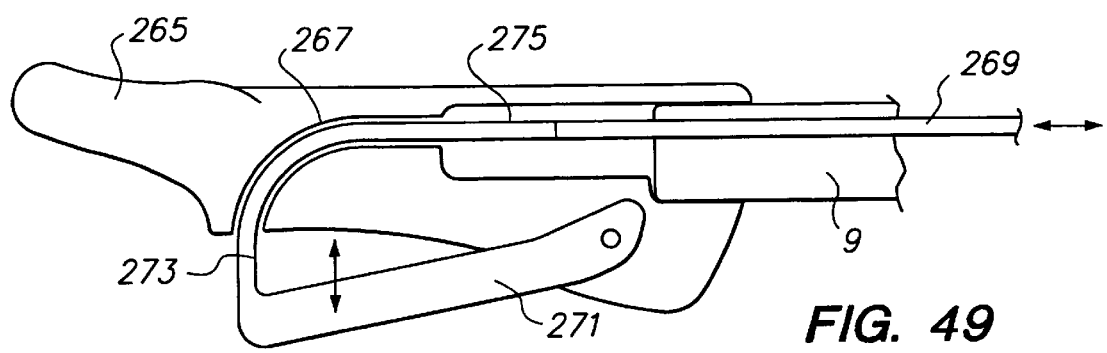
FIG. 49 is a partial cutaway sectional view of another embodiment of a hand-operated mechanism on a proximal end of a cannula.

In another embodiment as illustrated in FIG. 49, housing 265 is attached to the proximal end of the cannula body 9, and includes therein a passageway 267 that is curved into substantial alignment with the body and an actuator rod 269 that is slidable therein, and into substantial alignment with the movement at the proximal end of the trigger element 271. An integral and flexible portion 273 of the trigger element 271 is thus slidable within the passageway 267 and is coupled 275 to the actuator rod 269 at the proximal end thereof to cause squeezing motion of the trigger element 271 toward the housing 265 to translate into axial sliding movement of the rod 269 within a lumen of the body 9. The trigger element 271 and integral portion 273 may be molded of a suitable plastic material to provide requisite flexibility with only insignificantly compressible dimensions between the trigger element 271 and coupling 275 to the rod 269.

Figure 50:
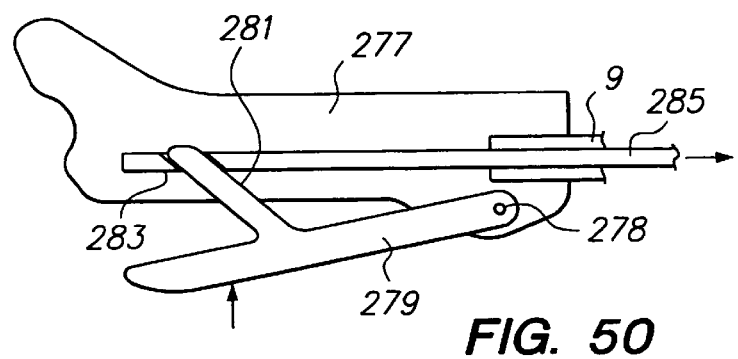
FIG. 50 is a partial cutaway sectional view of still another embodiment of a hand-operated mechanism on a proximal end of a cannula.

Referring now to FIG. 50, there is shown a housing 277 attached to the proximal end of a cannula body 9 and pivotally supporting 278 a trigger element 279 thereon that includes an integral camming portion 281 which engages a slot 283 in actuator rod 285. The camming portion 281 of the trigger element 279 is slanted relative to a radius from the pivot 278 to translate squeezing motion on the trigger element toward the housing 277 into sliding motion of the actuator rod 285 within a lumen of the body 9.

Figure 51:
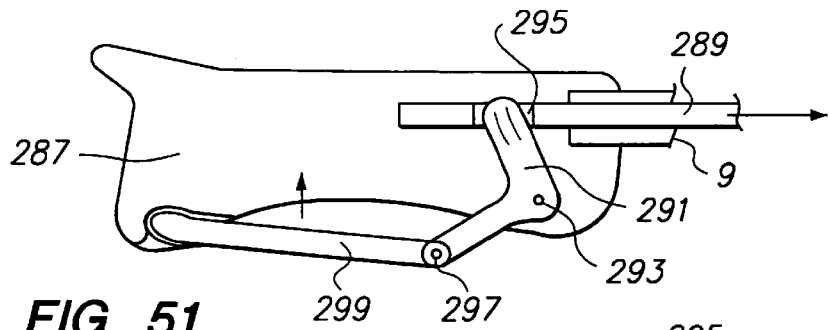
FIG. 51 is a partial cutaway sectional view of a hand-operated mechanism on the proximal end of a cannula.
Figure 52:
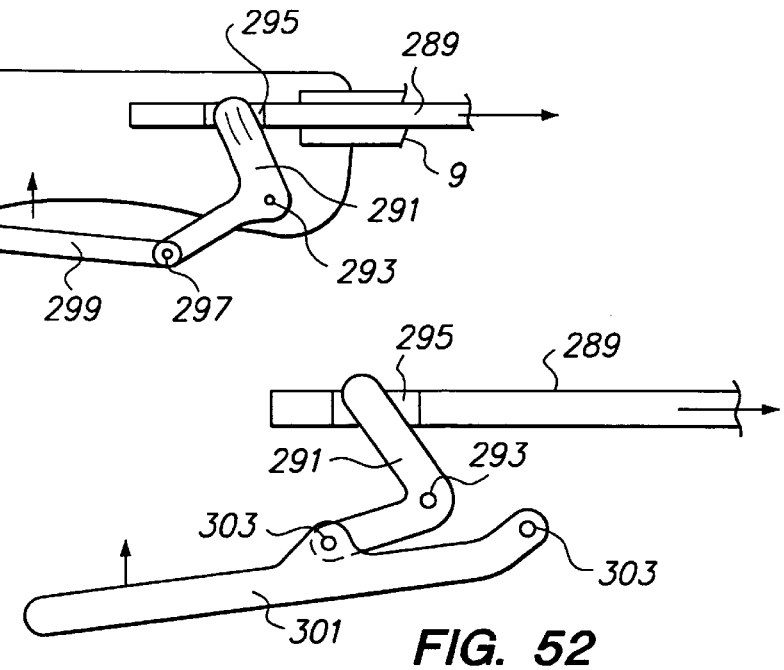
FIG. 52 is a partial cutaway sectional view of an alternative embodiment of the trigger element and assembly of FIG. 51.

Referring now to FIG. 51, there is shown another embodiment in which the housing 287 is attached to the proximal end of the cannula body 9. An actuator rod 289 is slidably disposed within a lumen of the body 9 and is coupled to the trigger element 291 that is pivoted 293 on the housing 287. The trigger element 291 includes an upper portion that couples to the actuator rod 289 within a slot 295 therein at approximately normal orientation relative to the rod 289. The trigger element also includes a lower portion that is hinged 297 to an auxiliary element 299 that is slidably pivoted in the housing 287. In this assembly, squeezing motion of the auxiliary element 299 is translated to rotational movement of the trigger element 291 about the pivot 293 which, in turn, causes sliding movement of the rod 289 within a lumen of the body 9. As illustrated in the embodiment of FIG. 52, a similar auxiliary element 301 may be pivoted 303 to a supporting housing and also pivotally hinged to the trigger element 291. In this assembly, low profile and mechanical leverage or advantage may be obtained from the squeezing motion on the auxiliary element 301 about the pivot 303 toward the supporting housing which is, in turn, coupled to the trigger element 291 for rotation thereof about the pivot 293. Such rotational motion of the trigger element 291 about pivot 293 is coupled to the actuator rod 289 via the slot 295 to slidably move the rod 289 within a lumen of a supporting cannula body.

Figure 53A:
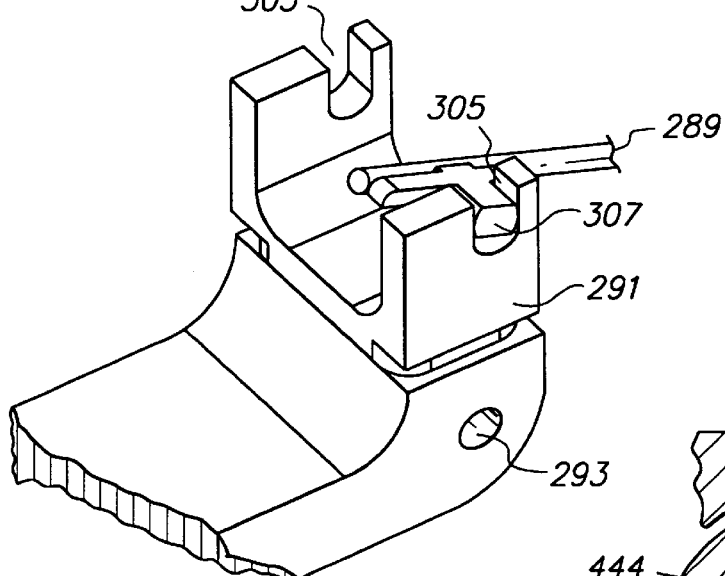
FIG. 53A is a partial perspective view of a coupling assembly in accordance with an alternative embodiment for coupling the trigger element and actuator rod of FIGS. 31, 40, 41, 51 or 52.
Figure 53B:
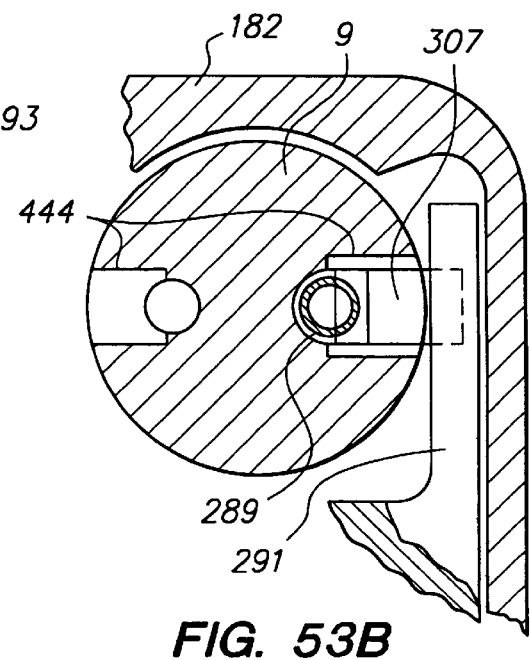
FIG. 53B is a sectional view of the trigger element and assembly of FIG. 53A within a housing.

Referring now to the perspective view of FIG. 53A, there is shown an embodiment of a trigger element such as 291 of FIG. 51 or 52 (or element 185 of FIG. 31, or element 212 of FIG. 40, or element 213 of FIG. 41) that includes a yoke-shaped upper portion including slots 305 in each arm of the yoke. An appendage of coupler 307 may be coupled (e.g., like element 241 in FIGS. 46, 47A or 47B, or like element 203 in FIGS. 38, 40 or 41) to the actuator rod 289 (or the proximal end of the rod 289 may be bent laterally) to form a lateral protrusion that is engaged within the slot 305 to couple rotational movement of the element 291 about the pivot 293 into translational movement of the rod 289. The body of coupler 307 slides with the actuator rod 289 in a slot 444 in the cannula body 9 at a location adjacent to the actuator rod 289, as illustrated in the partial sectional view of FIG. 53B, in order to avoid transferring any rotational or vertical forces from the trigger 291 to the actuator rod 289. Dual, substantially parallel actuator rods 289 (one only illustrated) may be actuated in similar manner via the slots 305 in each arm of the yoke-shaped element 291.

In each of the embodiments disclosed herein of pivoted trigger elements, such pivoted rotation of the trigger element in response to manual manipulation thereof may be translated into rotational movement of the actuator rod within the body 9, as may be required for operating the assembly at the distal end of the body 9. Specifically, this may be accomplished, for example, by incorporating a portion or sector of a beveled pinion gear within the trigger element centered about the pivot axis thereof and in mating engagement within a beveled pinion gear attached to the actuator. Also, spring return of the assembly at the distal end of body 9 to the retracted position may be provided by the resilient, flexible sheath such as sheath 135, or by spring elements disposed in conventional manner between fixed and movable components of the assembly at the distal end, or of the assembly at the proximal end.

In operation, a cannula body 9 including elements near the distal end thereof that are selectably configurable in expanded and retracted positions in accordance with one of the embodiments disclosed herein may be inserted in tissue, for example, through a transdermal incision with the elements configured in retracted position. The tapered and slightly blunted tip 13 may be advanced into tissue to bluntly dissect an initial passage or channel therein from the location of the incision. The trigger element (185) near the proximal end of the cannula 9 in accordance with an embodiment disclosed herein is manually manipulated, or squeezed toward the adjacent housing in the user's hand to move the actuator rod that is linked thereto. The movement of the actuator rod re-configures the assembly near the distal end of the cannula toward the expanded position, thereby displacing adjacent tissue. Selectably relaxing the user's squeeze of the trigger element allows resilient return of the actuator rod and the elements linked thereto near the distal end of the cannula toward the retracted position. In such configuration, the cannula 9 may again be advanced into tissue to extend the channel or passage thus formed therein, and the trigger element may again be selectably squeezed and relaxed repeatedly in alternation with advances of the cannula into the tissue to selectively displace and bluntly dissect tissue along the channel or passage thus formed. With the direct mechanical linkage via the actuator rod between the configurable elements near the distal end, and the trigger element near the proximal end, a user attains tactile 'feel' of the tissue being dissected near the distal end of the cannula, and the transparent tip 13 facilitates visualization of the tissue being dissected, in the manner as previously described.

Therefore, the various embodiments of mechanical retractors illustrated and described above greatly facilitate selectively bluntly dissecting or otherwise displacing bodily tissue at a surgical site near the distal end of an elongated cannula body in response to manual manipulation of mechanical actuators near the proximal end of the cannula body. Direct mechanical linkage between such manual actuators and tissue retractors promotes direct tactile feedback to the surgeon during manipulation of the actuators concerning the condition of tissue at the surgical site near the distal end of the cannula. In addition, the mechanical retractors may be configured in a wide diversity of expansion patterns that may be more selective in bluntly dissecting tissue than merely the omni-radial expansion that is attained using conventional pressurizable bladders or balloons.

What is claimed is:

1. Tissue manipulating apparatus comprising:

an elongated body having a distal end and a proximal end, and having a lumen therein disposed within the body substantially between the ends thereof;

an actuator movably disposed along the body substantially between the ends of the body;

a tissue-dissecting tip attached to the distal end of the body;

an arm disposed near the distal end of the body for selective outward movement of an end thereof relative to the body;

auxiliary means disposed near the distal end of the body to engage the arm at a selected location thereon for relative movement with respect thereto to move the arm outwardly relative to the body;

an element coupling the actuator near the distal end of the body to impart relative motion between the arm and auxiliary means to elevate the arm outwardly from the body in response to motion of the actuator relative the body; and a manual actuator disposed near the proximal end of the body and coupled to the actuator for moving the actuator relative to the body in response to manual manipulation of the manual actuator.

2. The apparatus according to claim 1 in which the body includes a surface recess near the distal end thereof and in which the auxiliary means is mounted within the recess for movement relative to the arm for engaging the arm to move the arm outwardly relative to the body.

3. The apparatus as in claim 1 wherein the arm is pivoted near the distal end of the body, and the auxiliary means is disposed for slidable movement toward the distal end of the body to move the arm outwardly relative to the body in response thereto.

4. The apparatus according to claim 1 in which the body includes another lumen therein for slidably receiving an endoscope therein, and wherein said tissue-dissecting tip is transparent and is disposed at the distal end of the body to permit visualization of tissue through the tip via an endoscope within said another lumen.

5. The apparatus according to claim 4 in which the body includes an auxiliary lumen therein eccentric said another lumen; and said tip includes a port therethrough in alignment with said auxiliary lumen.

6. The apparatus according to claim 1 including a plural number of said arms disposed near the distal end of the body at selected angular displacements about the body; and the auxiliary means engages the plurality of arms for relative movement with respect thereto to move the arms outwardly relative to the body.

7. The apparatus as in claim 1 in which said auxiliary means includes an auxiliary arm arranged in substantial axial alignment with the arm near the distal end of the body for relative movement with respect to said arm and linked thereto at a location over the length of the arm for moving outwardly relative to the body with the arm in response to relative motion of the arm and auxiliary arm.

8. The apparatus as in claim 7 in which an end of the auxiliary arm is secured against movement axially along the body, and an opposite end of the auxiliary arm is disposed to engage with said arm at a location intermediate the ends of said arm;

said arm is movable axially along the body relative to the auxiliary arm for moving outwardly relative to the body with said auxiliary arm engaged with said arm.

9. The apparatus as in claim 8 including a ramp element disposed relative to the auxiliary arm to elevate the auxiliary arm outwardly relative to the body in response to movement of the actuator.

10. The apparatus according to claim 9 in which the ramp element and arm move substantially simultaneously in response to movement of the actuator.

11. The apparatus as in claim 7 in which an end of the arm is secured against movement axially along the body, and an end of the auxiliary arm is disposed to engage the arm at a location intermediate the ends thereof;

said auxiliary arm is movable axially along the body relative to the arm for moving outwardly relative to the body which said arm engaged therewith.

12. The apparatus as in claim 11 including a ramp element disposed relative to the auxiliary arm to elevate the auxiliary arm relative to the body in response to movement of the actuator.

13. The apparatus as in claim 7 in which a portion of the length of the arm near the end thereof that moves outwardly relative to the body overlays the auxiliary arm in the retracted position of arm and auxiliary arm adjacent the body.

14. The apparatus as in claim 7 in which adjacent ends of the arm and auxiliary arm are linked for movement outwardly relative to the body in response to relative movement of the opposite ends thereof substantially in an axial direction along the body.

15. The apparatus as in claim 14 including a saddle element disposed near the adjacent ends of the arm and auxiliary arm for moving outward from the body therewith in response to said relative movement of said opposite ends of the arm and auxiliary arm.

16. The apparatus as in claim 15 in which said saddle element links said adjacent ends for outward movement of the arm and auxiliary arm with lateral rigidity relative to the axial extend of the body.

17. The apparatus as in claim 1 in which the arm includes a portion of the length thereof near the end thereof that moves outward relative to the body that exhibits greater flexibility than a portion of the length of the arm near the opposite end thereof.

18. The apparatus as in claim 17 in which the portion of the arm exhibiting greater flexibility includes a plurality of cuts forming segments of reduced cross section in directions substantially normal to the axial extent of the body.

19. The apparatus as in claim 1 including a sheath of resilient, flexible material disposed about the arm and a portion of the body near the distal end thereof.

20. Tissue manipulating apparatus comprising:

an elongated body having a distal end and a proximal end, and including a tissue-manipulating assembly near the distal end of the body;

an actuator movably disposed with respect to the body substantially between the ends thereof and coupled to the assembly for manipulating tissue in response to movement of the actuator relative to the body;

a housing attached to the body near the proximal end of the body;

a trigger element mounted for movement in a plane of the elongated body relative to the housing in response to manual manipulation of the trigger element; and a coupling mechanism disposed in communication with the trigger element and with the actuator for moving the actuator relative to the body in response to manual manipulation of the trigger element relative to the housing.

21. The apparatus according to claim 20 in which the housing is configured to be contained within the palm of a user; and said trigger element includes a lever spaced away from the housing and disposed substantially in alignment with the body for movement in the plane of the elongated body about pivot axis supported by the housing in response to manual manipulation of the lever; and said coupling mechanism translates pivoted movement of the lever about the pivot axis to sliding movement of the actuator relative to the body.

22. The apparatus according to claim 21 in which the trigger element includes a yoke-shaped segment having spaced arms disposed on opposite sides of the actuator in substantially normal orientation with respect thereto; and the coupling element engages the arms and the actuator for sliding the actuator relative the body in response to manual manipulation of the lever toward the housing.

23. A method for displacing tissue using a bluntly dissecting elongated cannula having configurable elements near the distal end thereof that are selectably configurable in expanded and retracted positions in response to mechanical movement of an actuator controlled by manual manipulation of a trigger element mounted near the proximal end of the cannula for movement within a plane of the elongated cannula, the method comprising:

a) inserting the distal end of the cannula into tissue to be dissected with the elements configured in retracted position;

b) advancing the cannula to bluntly dissect a passage in tissue;

c) selectively manually manipulating the trigger element within the plane of the elongated cannula to mechanically move the actuator relative to the cannula from one orientation thereof toward another orientation thereof for selectably configuring the elements in expanded position near the distal end of the cannula to expand the bluntly-dissected passage in the tissue, and then to mechanically move the actuator from the other orientation thereof toward said one orientation thereof for configuring the elements in the retracted position near the distal end of the cannula; and selectively repeating steps b) and c) to displace tissue bluntly dissected by the cannula along a selected course.

24. A method for endoscopic harvesting of a blood vessel using an elongated cannula having a tip on a distal end for bluntly dissecting tissue and having a portion of the elongated cannula near the distal end that is mechanically alterable between expanded and retracted configurations, the method comprising:

forming an incision in skin overlying the vessel to expose the vessel;

inserting the tip of the cannula in the incision adjacent the exposed vessel;

advancing the tip of the cannula in retracted configuration along the course of the vessel to dissect tissue and separate the vessel from surrounding tissue to form a cavity adjacent the vessel;

selectively reconfiguring the cannula to expanded configuration at locations along the vessel to expand the cavity adjacent the vessel;

sealing the incision and insufflating the cavity with fluid under pressure;

occluding and cutting side branches from the vessel along a length thereof within the cavity; and sealing and cutting the vessel at spaced locations therealong within the cavity for removal through the incision.

25. The method according to claim 24 performed with the elongated cannula in which said portion thereof near the end includes at least one extension element disposed to translate between retracted and expanded configurations in response to movement of an elongated actuator coupled thereto that is carried by the cannula between a proximal end thereof and the distal end, the method wherein:

said reconfiguring of the cannula is manually controlled at selected locations along the vessel in response to movement of the actuator initiated from near the proximal end of the cannula, as the tip at the distal end of the cannula proceeds in a selected direction along the course of the vessel to provide said expansion of the cavity in response to said reconfiguration of the cannula.

26. A method for endoscopic harvesting of a blood vessel using an elongated cannula having a tip on a distal end for bluntly dissecting tissue and having a portion of the elongated cannula near the distal end that is mechanically alterable between expanded and retracted configurations, the method comprising:

forming an incision in the skin overlying the vessel to expose the vessel and form an initial cavity;

sealing the incision and insufflating the cavity with fluid under pressure;

advancing the tip of the cannula along the course of the vessel to dissect tissue and separate the vessel from surrounding tissue to extend the cavity adjacent the vessel;

selectively reconfiguring the cannula to expanded configuration at locations along the vessel to expand the cavity adjacent the vessel;

occluding and cutting side branches from the vessel along a length thereof; and sealing and cutting the vessel at spaced locations therealong within the cavity for removal through the incision.

27. The method according to claim 25 performed with the elongated cannula in which said portion thereof near the distal end includes at least one extension element disposed to translate between retracted and expanded configurations in response to movement of an elongated actuator coupled thereto that is carried by the cannula between a proximal end thereof and the distal end, the method wherein:

said reconfiguring of the cannula is manually controlled at selected locations along the vessel in response to movement of the actuator initiated from near the proximal end of the cannula, as the tip at the distal end of the cannula proceeds in a selected direction along the course of the vessel to provide said expansion of the cavity in response to said reconfiguration of the cannula.

* * * * *